(12) United States Patent
Ekström et al.

(10) Patent No.: US 12,357,240 B2
(45) Date of Patent: Jul. 15, 2025

(54) MACHINE LEARNING ANALYSIS TECHNIQUES FOR CLINICAL AND PATIENT DATA

(71) Applicant: Kaiku Health Oy, Helsinki (FI)

(72) Inventors: Jussi Ekström, Helsinki (FI); Henri Virtanen, Helsinki (FI); Santeri Mentu, Helsinki (FI)

(73) Assignee: Kaiku Health Oy, Helsinki (FI)

( * ) Notice: Subject to any disclaimer, the term of this patent is extended or adjusted under 35 U.S.C. 154(b) by 392 days.

(21) Appl. No.: 17/819,576

(22) Filed: Aug. 12, 2022

(65) Prior Publication Data

US 2023/0048995 A1 Feb. 16, 2023

Related U.S. Application Data

(60) Provisional application No. 63/260,243, filed on Aug. 13, 2021.

(51) Int. Cl.
*A61B 5/00* (2006.01)
*G16H 50/50* (2018.01)
(52) U.S. Cl.
CPC .......... *A61B 5/7275* (2013.01); *A61B 5/4842* (2013.01); *A61B 5/4848* (2013.01); *A61B 5/7267* (2013.01); *G16H 50/50* (2018.01)
(58) Field of Classification Search
CPC ... A61B 5/7275; A61B 5/4842; A61B 5/4848; A61B 5/7267; G16H 50/50; G16H 20/40; G16H 30/40; G16H 40/63; G16H 50/20; G16H 10/20; A61N 5/103
See application file for complete search history.

(56) References Cited

U.S. PATENT DOCUMENTS

| 10,475,539 | B2 * | 11/2019 | Rubenstein | ............ G16H 50/20 |
| 2019/0362819 | A1 | 11/2019 | Virtanen et al. | |
| 2020/0227168 | A1 * | 7/2020 | Kimmerling | ............ G06N 5/01 |

OTHER PUBLICATIONS

"Predicting Onset and Continuity of Patient-Reported Symptoms in Patients Undergoing Immune Checkpoint Inhibitor (ICI) Therapies Using Machine Learning", (2019), 1 pg.

(Continued)

*Primary Examiner* — Scott M. Getzow
(74) *Attorney, Agent, or Firm* — Schwegman Lundberg & Woessner, P.A.

(57) ABSTRACT

Systems and methods are disclosed for analyzing data from oncology treatments such as immune checkpoint inhibitor or radiotherapy therapies, including predicting adverse events of the oncology therapies, predicting objective response of the oncology therapies, predicting symptoms from the oncology therapies, and use of such predictions by technological implementations to achieve improved system and medical outcomes. An example technique for generating a predicted treatment outcome includes: receiving patient data for a human subject, which provides patient-reported outcomes collected from the human subject relating to a particular oncology treatment; processing the patient data with a trained artificial intelligence (AI) prediction model, which receives the patient data as input and produces a prediction of a treatment outcome as output; and outputting data to modify a treatment workflow of an oncology treatment for the human subject, based on the prediction of the treatment outcome.

32 Claims, 22 Drawing Sheets

(56) References Cited

OTHER PUBLICATIONS

Amatriain, Xavier, "NLP and Healthcare: Understanding the Language of Medicine", [Online]. Retrieved from the Internet: URL: https: medium.com curai-tech nlp-healthcare-understanding-the-language-of-medicine-e9917bbf49e7, (Nov. 5, 2018), 21 pgs.

IIvanainen, S, "Predicting the onset of immune-related adverse events (irAEs) in immune checkpoint inhibitor (ICI) therapies using a machine learning (ML) model trained with electronic patient-reported outcomes (ePROs) and lab measurements", Department of Oncology and Radiotherapy,Oulu University Hospital (OYS), MRC Oulu, Oulu, FinlandKaiku Health, Helsinki, Finland, (2020), 1 pg.

IIvanainen, S, "A combination model of electronic patient-reported outcomes (ePROs) and lab measurements in prediction of immune related adverse events (irAEs) and treatment response of immune checkpoint inhibitor (ICI) therapies", Department of Oncology and Radiotherapy, Oulu University Hospital (OYS), MRC Oulu, Oulu, Finland Kaiku Health, Helsinki, Finland, (2020), 1 pg.

Livanainen, S.M. E, "Predicting objective response rate (ORR) in immune checkpoint inhibitor (ICI) therapies with machine learning (ML) by combining clinical and patient-reported data", Annals of Oncology vol. 31 Issue S7, (2020), 1 pg.

Kononen, Juha, "Machine learning (ML) for predicting patient-reported symptoms during breast and prostate radiotherapy (RT)", Oncology, Docrates Cancer Center, Helsinki, FinlandMedical Science, Kaiku Health Ltd, Helsinki, FinlandInstitut fur Radiotherapie Aarau, Aarau, Switzerland, (2021), 1 pg.

Kononen, Juha, "Machine learning (ML) for predicting patient-reported symptoms during breast and prostate RT", [Online]. Retrieved from the Internet: URL: https: www.estro.org Congresses ESTRO-2021 609 posterdiscussion33-miscellaneous 3703 machinelearning-ml-forpredictingpatient-reportedsy, (May 8, 2021), 2 pgs.

Livanainen, S.M. E, "Predicting objective response rate (ORR) in immune checkpoint inhibitor (ICI) therapies with machine learning (ML) by combining clinical and patient-reported data", 38P Annals of Oncology vol. 31—Issue S7, (2020), 1 pg.

Livanainen, S.M. E, "Predicting onset and continuity of patient-reported symptoms in cancer patients undergoing immune checkpoint inhibitor (ICI) therapies using machine learning", 50P Annals of Oncology Clinical Practice vol. 30 Supplement 11, (Dec. 2019), 1 pg.

Livanainen, S.M. E, "A combination model of electronic patient-reported outcomes (ePROs) and lab measurements in prediction of immune related adverse events (irAEs) and treatment response of immune checkpoint inhibitor (ICI) therapies", 1876P Annals of Oncology vol. 31 Issue S4, (2020), 1 pg.

\* cited by examiner

101C

23.26

* IN THE PAST 7 DAYS, HAVE YOU HAD PAIN IN THE TREATMENT AREA?

◉ YES

○ NO

*142*

*141*

* WHAT HAS BEEN THE SEVERITY OF YOUR PAIN ON A SCALE FROM 0 TO 10?

7

NO PAIN     WORST PAIN YOU CAN IMAGINE

*143*

* HAVE YOU TAKEN MEDICATION TO EASE THE PAIN?

○ YES

SYMPTOMS THAT REQUIRE IMMEDIATE ATTENTION

*151*

PAIN (!) ALTHOUGH NOT VERY COMMONLY, RADIOTHERAPY MAY CAUSE PAIN TO THE TREATMENT AREA (SKIN, SUBCUTANEOUS TISSUE). FOR MILD/MODERATE PAIN YOU CAN TRY OVER-THE-COUNTER PAIN MEDICATION.

IF THE PAIN IS PERSISTING AND IS NOT RELIEVED WITH REGULAR PAIN MEDICATION IT MAY BE NECESSARY TO USE STRONGER PAIN MEDICATION AVAILABLE ONLY THROUGH PRESCRIPTION. PLEASE, CONTACT YOUR CARE TEAM.

FIG. 1D

| WEEK | WEEK 5 | WEEK 6 | WEEK 7 | WEEK 8 | WEEK 9 | WEEK 10 | WEEK 11 | WEEK 12 | WEEK 13 | WEEK 14 | WEEK 15 | WEEK 16 | WEEK 17 | WEEK 18 | WEEK 19 | WEEK 20 | WEEK 21 |
|---|---|---|---|---|---|---|---|---|---|---|---|---|---|---|---|---|---|
| ABDOMINAL PAIN | 0 | 0 | 0 | 0 | 0 | 0 | 0 | 0 | 0 | 0 | 0 | 0 | 0 | 0 | 0 | 0 | 23% |
| COUGH | 2 | 2 | 0 | 1 | 0 | 0 | 1 | 0 | 0 | 0 | 0 | 1 | 0 | 0 | 0 | 0 | 18% |
| DECREASED APPETITE | 0 | 1 | 1 | 0 | 0 | 0 | 0 | 0 | 0 | 1 | 0 | 2 | 0 | 0 | 0 | 0 | 6% |
| DIARRHEA | 1 | 0 | 0 | 0 | 1 | 1 | 1 | 0 | 2 | 1 | 1 | 0 | 0 | 0 | 1 | 3 | 82% |
| FATIGUE, TIREDNESS, LACK OF ENERGY | 2 | 1 | 0 | 0 | 2 | 1 | 1 | 1 | 0 | 0 | 1 | 0 | 1 | 1 | 2 | 0 | 62% |
| ITCHING | 0 | 0 | 0 | 0 | 0 | 0 | 0 | 0 | 0 | 0 | 0 | 0 | 0 | 0 | 0 | 0 | 31% |
| JOINT PAIN | 0 | 0 | 0 | 0 | 0 | 0 | 0 | 0 | 0 | 0 | 0 | 0 | 0 | 0 | 0 | 0 | 6% |
| NAUSEA | 0 | 0 | 1 | 1 | 0 | 0 | 0 | 0 | 0 | 0 | 0 | 0 | 0 | 0 | 0 | 0 | 23% |
| RASH | 0 | 0 | 0 | 1 | 0 | 0 | 0 | 0 | 0 | 0 | 0 | 1 | 1 | 1 | 1 | 1 | 74% |

FIG. 10A

MACHINE LEARNING ANALYSIS TECHNIQUES FOR CLINICAL AND PATIENT DATA

PRIORITY CLAIM

This application claims the benefit of priority to U.S. Provisional Patent Application No. 63/260,243, filed Aug. 13, 2021, which is incorporated by reference herein in its entirety.

BACKGROUND

Immune checkpoint inhibitor (ICI) therapies, a type of immunotherapy, work by enhancing the immune system's ability to recognize and attack cancer cells. While ICIs are a standard of care in several cancer types, they have introduced novel toxicities which differ from conventional therapies. In particular, immune-related adverse events (irAEs) can arise from various organ systems, and at any time during or after the discontinuation of ICI therapy. irAEs can be severe and even life threatening, but if caught and treated early, most of them are reversible. Thus, early detection of irAEs can result in an improved safety profile of ICI treatments and an improved quality of life for cancer patients.

ICIs are used as treatments in several malignancies, both in adjuvant and advanced settings. However, the treatment response assessment of ICIs differs from traditional cancer therapies, due to unique tumor response patterns such as pseudo- and hyper-progression. Furthermore, the temporal association of radiological response to treatment may sometimes be obscure. While only a subset of patients respond to ICIs, improved tools to assess the treatment response are needed to improve patient-care and clinical value of ICIs.

Radiation therapy (or "radiotherapy") is another standard of care treatment for malignancies. One such radiotherapy technique is provided using a Gamma Knife, by which a patient is irradiated by a large number of low-intensity gamma rays that converge with high intensity and high precision at a target (e.g., a tumor). Another such radiotherapy technique is provided using a linear accelerator (LINAC), whereby a tumor is irradiated by high-energy particles (e.g., electrons, protons, ions, high-energy photons, and the like). The placement and dose of the radiation beam is accurately controlled to ensure the tumor receives the prescribed radiation, and the placement of the beam is designed to minimize damage to the surrounding healthy tissue, often called the organ(s) at risk (OARs). Nonetheless, adverse events, side effects, and complications in the surrounding healthy tissue and other anatomical areas may result from radiotherapy treatment.

OVERVIEW

A first aspect discussed herein relates to predicting the onset of immune-related adverse events (irAEs) in immune checkpoint inhibitor (ICI) therapies using a machine learning (ML) model trained with electronic patient-reported outcomes (ePROs) and lab measurements. To be able to better predict the onset of irAEs, electronic patient-reported outcomes (PROs) combined with other clinical data can be used to develop machine learning (ML) based prediction models for irAEs and other types of adverse events (AEs). As detailed in the following examples, a digital platform may be used in a real world setting to capture symptom data from patients undergoing ICI therapies, to provide data for training and use of a ML model. For instance, anonymized and aggregated ePRO data may be combined with laboratory measurements to train a ML model to predict AE onset.

A second aspect discussed herein relates to predicting an objective response rate (ORR) in ICI or similar therapies with ML, by combining clinical and patient-reported data. The prognostic role of irAEs implies that a niche of patients who can benefit from ICIs could be identified. A comprehensive and timely assessment of patient symptoms undergoing ICI therapies is feasible via ePRO collection. As noted above, ePRO data can be combined with other clinical data sources to generate ML based models which predict irAEs (or other AEs) and analyze related data. As a result, an ORR can be produced in patients undergoing ICIs for advanced cancers, using clinical and ePRO data as an input for training and use of a ML model.

A third aspect discussed herein relates to the prediction and evaluation radiotherapy-related symptoms from patients undergoing radiotherapy treatment. Characteristics such as occurrence and severity of symptoms and AEs related to treatment toxicities may be collected from ePROs during and after radiotherapy treatment, and analyzed with a trained ML model. This ML model may provide insights on the patient experience, which among other benefits, can be used to increase the feeling of safety in patients and improve the overall quality of patient care. As will be understood, the prediction of radiotherapy-related symptoms can enable earlier interventions, modifications to radiotherapy treatment and planning processes, improved treatment safety, and improved quality of life for patients.

An example method, computer-readable medium, or computing system implementation of such aspects is provided with operations for generating a predicted treatment outcome of an oncology treatment for a human subject. Such operations include: receiving patient data for the human subject, with such patient data including patient-reported outcomes relating to the oncology treatment that are collected from the human subject; processing the patient data with a trained artificial intelligence (AI) prediction model, with this trained AI prediction model being previously configured (e.g., trained) to receive the patient data as an input and to produce a prediction of a treatment outcome for the human subject as an output; and outputting data (e.g., commands, messages, selections, recommendations, or other electronic outputs) to modify a treatment workflow of the oncology treatment for the human subject, based on the prediction of the treatment outcome. A variety of systems or users (e.g., an oncology information system, an overseeing oncologist) may utilize such data to implement the modification of the treatment workflow for the human subject.

In some examples of this implementation, the prediction of the treatment outcome includes a prediction of one or more adverse events, such that the prediction of each respective adverse event includes: a probability of an occurrence of the respective adverse event, and a timing and a severity of the respective adverse event, if the probability of the occurrence of the respective adverse event exceeds a defined amount.

In further examples of this implementation, the one or more adverse events are radiotherapy adverse events, the oncology treatment is a radiotherapy treatment, and the data to modify the treatment workflow includes a command to change (or, a recommendation to change) a plan used for delivering the radiotherapy treatment to the human subject based on the radiotherapy adverse events. For instance, a timing, a dosage, or a location of the radiotherapy treatment, to be delivered with the plan, may be changed based on the prediction of the radiotherapy adverse events.

In other further examples of this implementation, the one or more adverse events are immune-related adverse events, the oncology treatment is an immune checkpoint inhibitor therapy, and the data to modify the treatment workflow includes a command to change (or, a recommendation to change) an amount or a timing of an immunotherapy treatment delivered to the human subject with the immune checkpoint inhibitor therapy.

In some examples, the prediction of the treatment outcome includes a prediction of an objective response rate of the human subject to the oncology treatment, such that the prediction of the objective response rate includes an indication or classification of a complete response or an amount of a partial response to the oncology treatment.

In some examples, the patient-reported outcomes are provided from structured data collected in a questionnaire, using a questionnaire that provides a series of questions that is customized to the human subject. Alternatively or in addition, the patient-reported outcomes are provided from unstructured data collected in one or more text inputs of the questionnaire.

In some examples, the patient data includes one or more of: clinical information of the human subject; laboratory data from one or more specimens collected from the human subject; treatment information from prior sessions of the oncology treatment delivered to the human subject; measurements from one or more wearable devices used by the human subject; measurements from one or more medical monitoring devices external to the human subject; or event data from prior occurrence of adverse events by the human subject.

In some examples, the trained AI prediction model uses an extreme gradient boosting supervised machine learning algorithm. Further, additional operations may include verifying performance of the trained AI prediction model after training, and before use with the patient data, based on one or more metrics including some combination of: accuracy, precision and recall, and a correlation coefficient. Also in some examples, the trained AI prediction model is trained with training data that is specific to the human subject and a type of the oncology treatment, and the patient data is collected between treatment sessions of the oncology treatment.

In some examples, processing the patient data with the trained AI prediction model includes use of multiple AI prediction models to produce the output, such as where each of the multiple AI prediction models is customized to a respective symptom or respective outcome associated with the oncology treatment.

In some examples, additional operations may be based on the prediction of the oncology treatment outcome, such as: outputting information related to the treatment outcome to the human subject or a clinician associated with the human subject, based on the prediction of the treatment outcome, with the information including one or more of: an alert, educational content, or a recommendation. Other electronic commands, data, or information may also be generated or communicated based on the prediction of the oncology treatment outcome.

In still additional examples, an example method, computer-readable medium, or computing system implementation may include performing analysis of the data of similar oncology treatments to identify patient-reported outcomes which may be indicative of problems, and then use the patient-reported data to identify where a plan delivery is inappropriate (or, to change the plan delivery). In such settings, an example method of monitoring efficacy of a treatment plan of a radiotherapy treatment for a human subject includes: processing the treatment plan with a trained artificial intelligence (AI) prediction model, the trained AI prediction model configured to receive data for the treatment plan as an input and to produce an adverse effect prediction report of potential adverse patient-reported outputs associated with the treatment plan indicative of ineffective treatment for the human subject as an output; receiving patient data for the human subject, the patient data including patient-reported outcomes relating to the treatment plan that are collected from the human subject; and monitoring for predicted adverse patient-reported outputs and, where identified, outputting data indicative that the treatment plan may require adjustment. Such output data may be used to determine whether delivery efficacy of the treatment plan is outside of acceptable parameters. Further, such output data may also modify a treatment workflow of the radiotherapy treatment for the human subject, based on a prediction of one or more outcomes of the radiotherapy treatment.

In still additional examples, an example method, computer-readable medium, or computing system implementation may include dynamically adapting a radiotherapy treatment plan having multiple fractions, based on a predicted treatment outcome of an oncology treatment for a human subject. Here, a method for dynamic adaption may include: developing or identifying a treatment workflow for the oncology treatment for the human subject based on clinically determined expected outcomes of such treatment; generating a predicted treatment outcome of the oncology treatment for the human subject; receiving intra-fraction patient data for the human subject, with such patient data including patient-reported outcomes relating to the oncology treatment that are collected from the human subject; processing the patient data with a trained artificial intelligence (AI) prediction model (e.g., a trained AI prediction model that is configured to receive the intra-fraction patient data as an input and to produce a prediction of a treatment outcome for the human subject as an output); comparing the predicted treatment outcome to an expected treatment outcome; and changing the treatment workflow based on the comparison of the predicted treatment outcome, in response to determining that a difference between the predicted treatment outcome and the expected treatment outcome is outside of a predetermined tolerance. In further examples, the patient reported outcomes (e.g., provided in the intra-fraction patient data) are utilized as input to enable a change to the treatment workflow.

The above overview is intended to provide an overview of subject matter of the present patent application. It is not intended to provide an exclusive or exhaustive explanation of the inventive subject matter. The detailed description is included to provide further information about the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

FIGS. 1A-1F illustrate user interfaces of a mobile device (e.g., smartphone) software application used to capture patient-reported symptom data, according to some examples.

FIGS. 10A and 10B illustrate user interfaces presenting a result of predicting a toxicity profile in connection with radiotherapy, according to some examples.

DETAILED DESCRIPTION

Figure 1A:
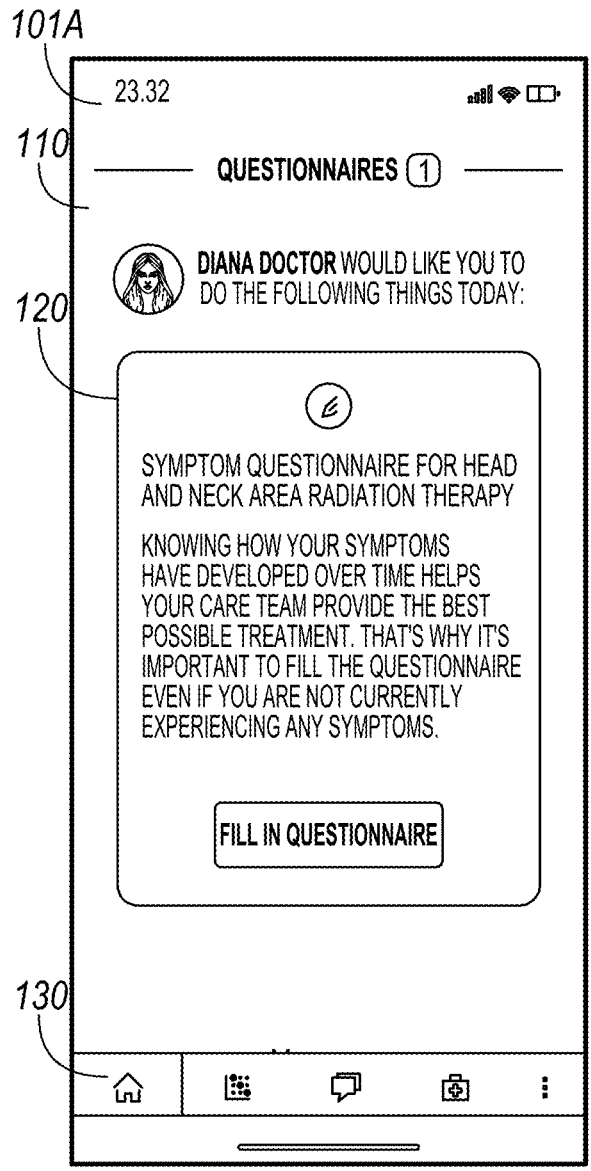

The following disclosure refers to techniques for (a) predicting immune-related adverse events (irAEs) or other adverse events (AEs) in oncology treatments such as immune checkpoint inhibitor (ICI) or radiation therapies; (b) predicting objective response rate (ORR) in oncology treatments such as ICI or radiation therapies; (c) predicting symptoms in oncology treatments in connection with radiation therapies (radiotherapy), and (d) use of such predictions by various technological implementations to achieve improved system operations and technical (and medical) outcomes. With these techniques, various technical systems can determine suitability of an oncology treatment, design or update a treatment plan for the oncology treatment, and change a treatment workflow for the oncology treatment.

Although some of these techniques are described separately for particular types of oncology therapies, ICI vs. radiation, it will be understood that data analysis techniques applicable to ICI therapies may also be applicable to radiation therapies (or other types of oncology treatments), and vice versa. These techniques are followed by a discussion of workflows, machine learning designs, and computing frameworks used for establishing and using the present techniques, as part of designing, monitoring, delivering, and updating medical treatments and related analysis of medical conditions and symptoms.

Predicting Adverse Events in ICI Therapies

In an example, the onset of irAEs in ICI therapies may be predicted using a machine learning (ML) model. Such a model may be trained with electronic patient-reported outcomes (ePROs) and lab measurements, and implemented with the following methods. Such a model may also be adapted for the consumption of other types of input data, such as medical device data or medical record data.

The data modeling methodology can follow a common classification approach used in machine learning. The classification problem may be defined to predict the binary outcome such as: (i) whether an irAE will onset in the upcoming 0-21 days, (ii) whether an irAE will not onset in the upcoming 0-21 days. Other types of outcomes may also be identified.

A ML prediction model may be trained to classify all data in one of a fixed number of categories (e.g., two categories, whether an irAE will onset or whether the irAE will not onset). The modeling framework for this data is explained in more detail in the flowchart of FIGS. 2A-2B, discussed below.

In an example implementation, a dataset which provides input data may be provided from three data sources:
(1) Multiple, different symptoms monitored with a digital platform, analyzing a total set of reported symptoms from treated patients (e.g., ICI treatments on advanced cancers).
(2) Laboratory data (including multiple, different values or data types) from analysis of specimens of the same patients during ICI therapy.
(3) Prospectively collected irAE data, including the onset and end dates, and the severity of irAEs. Severity can be assessed according to Common Terminology Criteria for Adverse Events (CTCAE).

FIGS. 1A to 1F provide user interfaces of a mobile device (e.g., smartphone) software application used to capture patient-reported symptom data from patients undergoing oncology therapies (e.g., radiotherapy, ICI therapy, etc.). Such interfaces may be used to collect data in a conversational (e.g., text chatbot) or questionnaire interface, which provides a series of questions. For instance, a questionnaire interface may offer questions that are displayed or change based on previous responses, as structured data is collected from a patient in the questionnaire answers. Also for instance, a questionnaire interface may offer an open-ended text field which is used to collect freeform, unstructured text answers or responses from a patient. Other interface types, including the collection of data from wearable devices, may also be used.

As an example, FIG. 1A depicts a user interface 101A which provides an interactive questionnaire 110. This questionnaire 110 specifically outputs interactive symptom information 120 whose information changes depending on user selections or inputs. A variety of interactive features of the user interface 101A (and user interfaces 101B, 101C, 101D, 101E, 101F) may be provided, including navigation controls 130, survey submission controls 131, messaging controls 132, and other forms of selectable inputs.

Figure 1B:
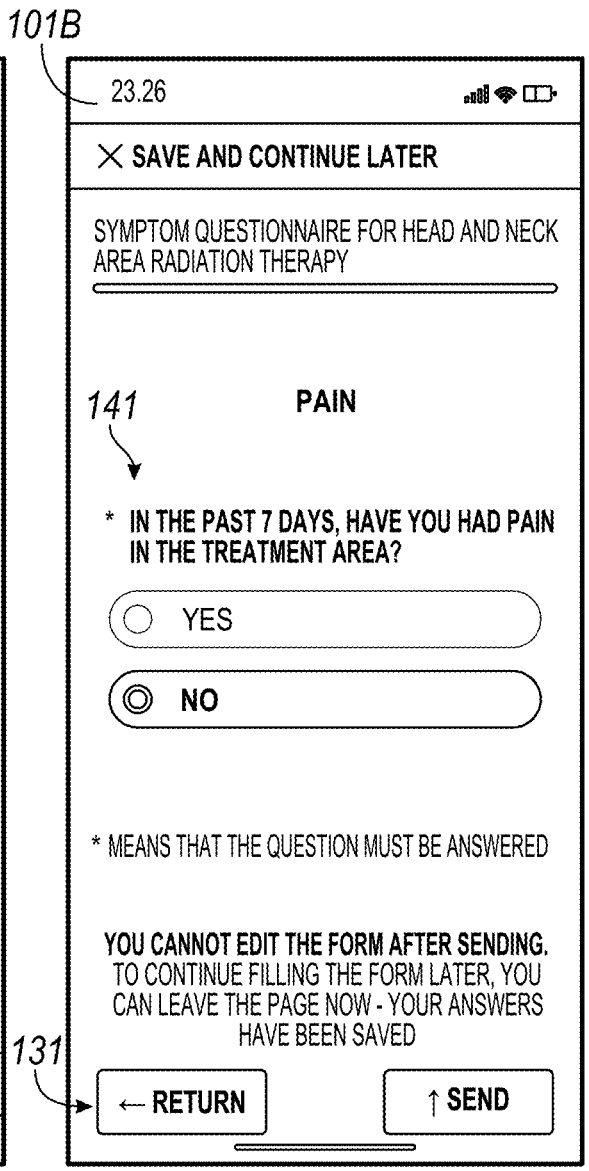

FIG. 1B continues with a progression of the user interface 101B, including a selectable (binary) question input control 141 (e.g., a radio form option). FIG. 1C continues with a progression of the user interface 101C, including a selectable (multi-choice) question input control 142 (e.g., a slider), and another selectable (binary) question input control 143 (e.g., a radio form option).

Figures 1E, 1F:
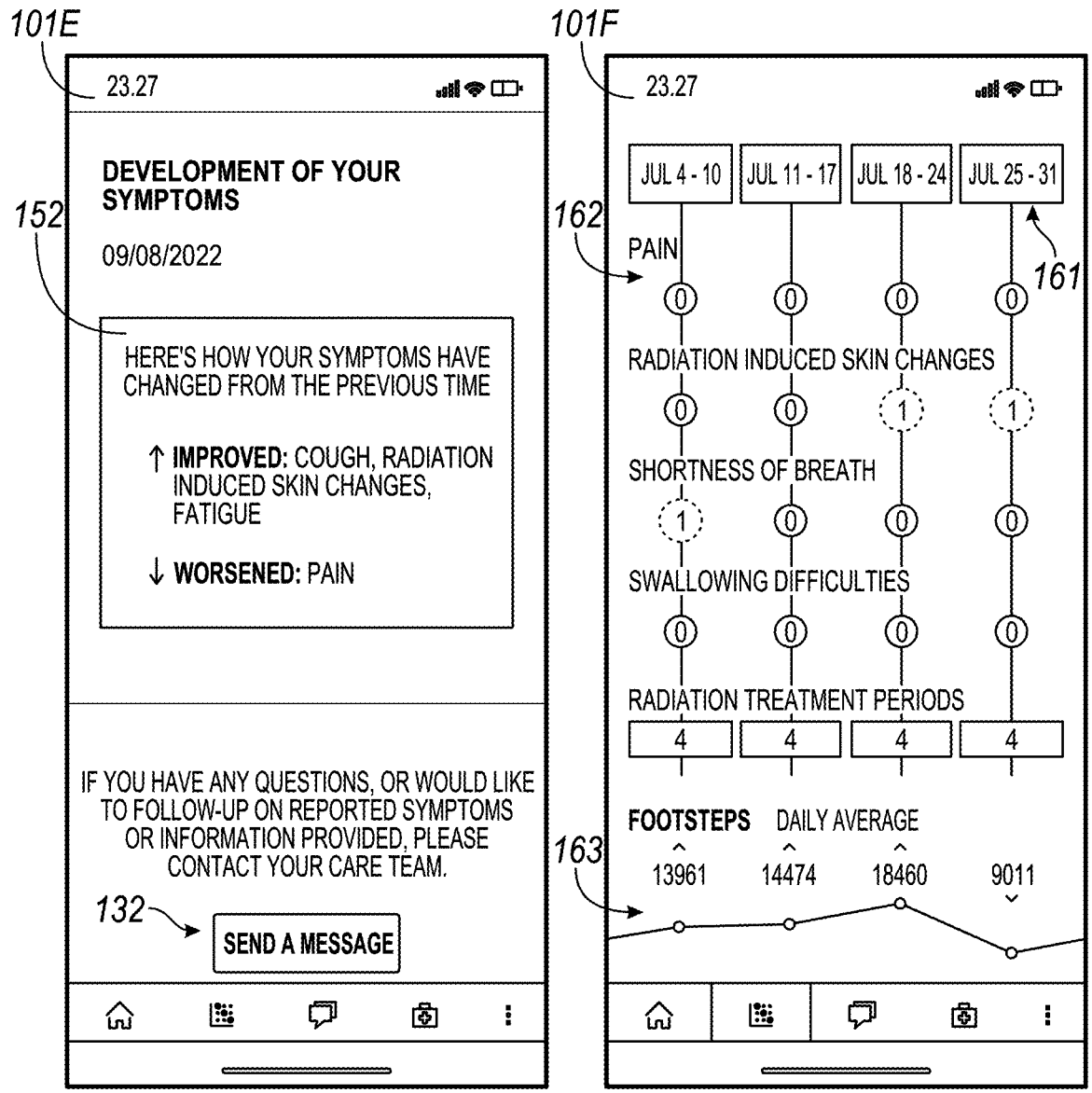

FIG. 1D continues with a progression of the user interface 101D to provide an output 151 from processing patient-reported outcomes in the interactive questionnaire (e.g., using the oncology data processing techniques discussed in more detail below). FIG. 1E continues with a progression of the user interface 101E to include a graphical illustration 152 for a prediction or analysis of a treatment outcome. Finally, FIG. 1F continues with a progression of the user interface 101F to graphically illustrate, during one or more time periods 161, measurements 162 of the patient-reported outcomes. This may be graphically correlated or compared to other information such as patient data measurements 163 from wearable devices (e.g., number of steps determined from a smart watch or phone).

The prediction model used for these and other analysis or predictions may be built using extreme gradient boosting (XGboost) which is a commonly used approach for classification problems. An important advantage of XGBoost is that it does not overfit easily, which is helpful as overfitting could risk the model's reliability with future predictions by learning training data too well, which leads to failure in classifying previously unseen data.

In an example, the ePRO and lab measurement data trains the prediction model to detect the onset (e.g., 0-21 days prior to diagnosis) of irAEs or other types of AEs. The dataset is split into training (e.g., 70% of the data) and test sets (e.g., 30% of the data), such as by random allocation. The test set can be left out from the model training and tuning, and used only to evaluate the model performance.

Performance of the trained prediction model can be evaluated using one or more metrics commonly used to assess classification models. These metrics may include the following:

TABLE 1

| Metric | Description | Values |
| --- | --- | --- |
| Accuracy | Describes how many predictions were correct as percentages. | 0-100% (e.g., 100% indicates perfect classification). |
| AUC | Describes how well a model can distinguish between two classes (objective response OR non-response). Common performance metric for binary classification. | Values between 0 and 1 (1 is perfect classification; 0.5 is random guessing) |
| F1 Score | Harmonic mean of two commonlyusedmetrics, precisionandrecall. Precision reveals what proportionofpositive | Values between 0 and 1 (1 indicates a perfect precision and recall) |

TABLE 1-continued

| Metric | Description | Values |
| --- | --- | --- |
| | identifications was actually correct and recall reveals what proportion of actual positives was identified correctly. | |
| MCC | Summarizes all possible cases for binary predictions: true and false positives and true and false negatives. Suitable for analyzing imbalanced datasets, where one class is rarer than the other. MCC produces a high score only if prediction performed well in all categories. | Values between −1 and 1 1 is a perfect classification, 0 is random guessing, and −1 indicates a completely contradictory classification. |

Figure 2A:
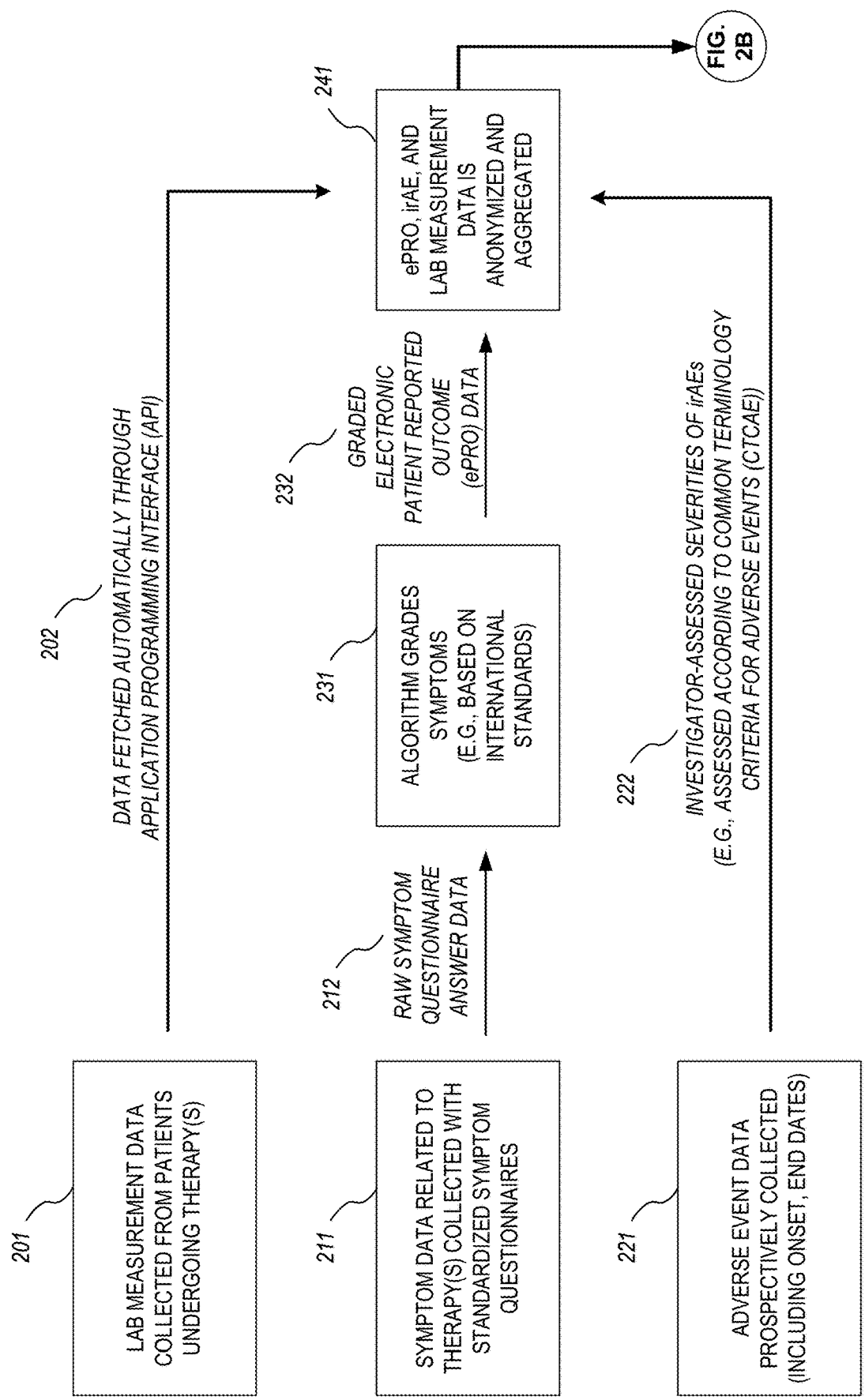
FIGS. 2A-2B illustrate a flowchart of a data modeling framework for predicting immune-related adverse events with use of immune checkpoint inhibitor therapies, according to some examples.
Figure 2B:
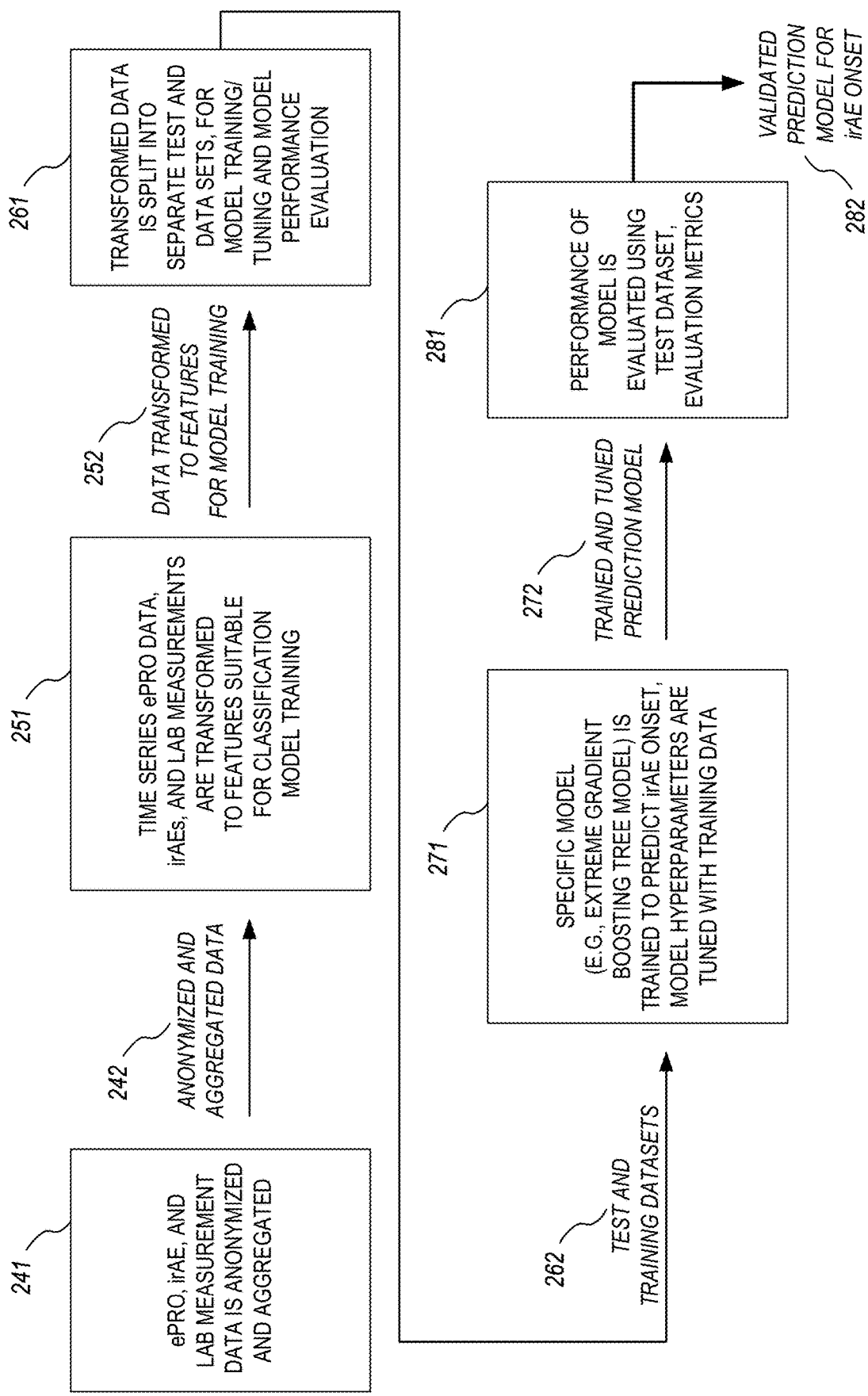

An example of the complete modeling framework is provided in the flowchart of FIGS. 2A-2B. FIG. 2A depicts a first portion and FIG. 2B depicts a second portion of this flowchart of a data modeling framework for predicting immune-related adverse events with use of immune checkpoint inhibitor therapies.

The flowchart begins in the example of FIG. 2A with the collection or receipt of three data sets: lab measurement data 201 collected from patients undergoing therapy (or therapies); symptom data 211 related to the therapy (or therapies) that has been collected with standardized symptom questionnaires; and adverse event data 221 that was prospectively collected from the patients (including onset and end dates). In an example, the lab measurement data 201 is collected from patients undergoing ICI therapies, and is the same group that reported symptoms in symptom data 211 and provides irAE data for the adverse event data 221. Also in an example, the questionnaires used to collect the symptom data 211 is based on the user interfaces and functions described with reference to FIGS. 1A to 1F. In the example of ICI therapies, such standardized PRO symptom questionnaires can be used to collect symptoms specifically related to ICI toxicities.

The data 201, 211, 221 can be provided, obtained, retrieved, or stored with various technical mechanisms. This may include, automatically retrieved lab measurement data 202 that is obtained through an application programming interface; and the retrieval of investigator-assessed severities of irAEs 222, such as irAEs that are assessed according to some standardized metric or standard such as the Common Terminology Criteria for Adverse Events (CTCAE).

Additional processing may be used to convert raw symptom questionnaire answer data 212 into graded electronic patient reported outcome (ePRO) data 232, such as with the use of an algorithm that grades individual symptoms of the raw data 212. Such grading may be based on some standardized metric or standard (such as international standards relevant to the condition or treatment). Ultimately, the results of the data, collected as ePRO data, irAE data, and lab measurement data, is anonymized and aggregated with various data functions 241 into an anonymized and aggregated data set 242.

Continuing with the flowchart of FIG. 2B, the anonymized and aggregated data set 242 can be additionally processed with a transformation function 251. Here, the time series ePRO data, irAEs, and lab measurements are transformed to features suitable for classification model training. Such features may include lab values as differences from baseline values and grades of the previously reported symptoms (e.g., scaled based on time between the questionnaires) and differences between the previously reported grades. The irAE data likewise may be used as labels. This produces a transformed data set 252, providing features for model training.

The transformed data set 252 is further processed at data processing function 261, which splits the data into separate test and training data sets for model training and tuning (training set), and for model performance evaluation (test set). This produces the test and training data sets 262. Then, a training function 271 operates to perform specific model training. For instance, an Extreme Gradient Boosting (XG-Boost) algorithm may be trained to predict irAE onset. The model hyperparameters may also be turned with the training data using repeated stratified cross-validation. This produces a trained and tuned prediction model 272.

The trained and tuned prediction model 272 may be evaluated with an evaluation function 281, which evaluates the performance of the model using the test data set and evaluation metrics. The evaluation metrics may include those discussed above in TABLE 1. This produces a validated prediction model 282, specifically trained and validated to predict irAE onset.

ML-based prediction models, trained with a dataset combined from multiple sources, ePRO data, investigator-assessed irAE data, and lab measurements, can predict the onset of irAEs with a high performance. Thus, ML models utilizing digital symptom monitoring data—combined with other clinical data sources—can enable early detection of irAEs in ICI treated cancer patients, ultimately improving the safety profile of the overall treatment.

Another application for irAE prediction models includes targeting toxicity management-related patient guidance individually, based on prediction model data. Likewise, another application for irAE prediction includes enhancing health care resource utilization by creating risk-based patient-follow-up schemes.

These predictive models may be developed further beyond the examples discussed above. For instance, the addition of more data on irAEs (or other medical AEs) may enhance the prediction model performance. Also, the use of additional data sources such as patient characteristics (e.g., from medical record data) and comorbidities can enhance the prediction model performance.

It will be understood that the results of such a configuration may also be verified, such as with a validation procedure that employs a larger dataset (e.g., from prospective clinical trials). After such validation, the potential clinical impact of irAE onset prediction models in catching immune-mediated toxicities can be evaluated and investigated on a wider scale.

Predicting Objective Response Rate in ICI Therapies

In an example, objective response rate (ORR) in ICI therapies may be predicted with machine learning (ML) by combining clinical and patient-reported data, as implemented with the following methods.

ORR may be defined as the proportion of patients in whom partial (PR) or complete (CR) responses are identified as a best overall response (BOR) according to some metric, such as Response Evaluation Criteria in Solid Tumors (RECIST 1.1). Stable disease (SD) was categorized as non-response together with progressive disease (PD).

A ML-based prediction model for ORR prediction can be built from data collected from multiple patients receiving the oncology treatment, e.g., with advanced cancers receiving ICI therapies. Several data sources may be used as inputs for the model:

(i) Clinician-assessed treatment responses according to the RECIST 1.1 metric;
(ii) Clinician confirmed irAEs according to some standard (e.g., Common Terminology Criteria for Adverse Events (CTCAE) v.5.0);
(iii) Patient-reported symptom data including multiple monitored symptoms collected using a digital platform;
(iv) Laboratory measurements from multiple, different tests (e.g., including blood tests for bilirubin, hemoglobin, ALP, ALT, platelets, leukocytes, creatinine, thyrotropin and neutrophils);
(v) Other variables: e.g., time from treatment initiation, age and sex.

Treatment responses and irAEs are collected prospectively. Closest preceding lab values and reported symptoms, both as changes from the baseline, are linked to the treatment responses. In addition, the model can be trained to account for whether the patient had had a diagnosed irAE prior/at the time of response evaluation.

In a specific example, the prediction model for ORR is built using extreme gradient boosting (XGBoost algorithm), which is a commonly used approach for classification problems. Other types of algorithms may also be used.

Figure 3A:
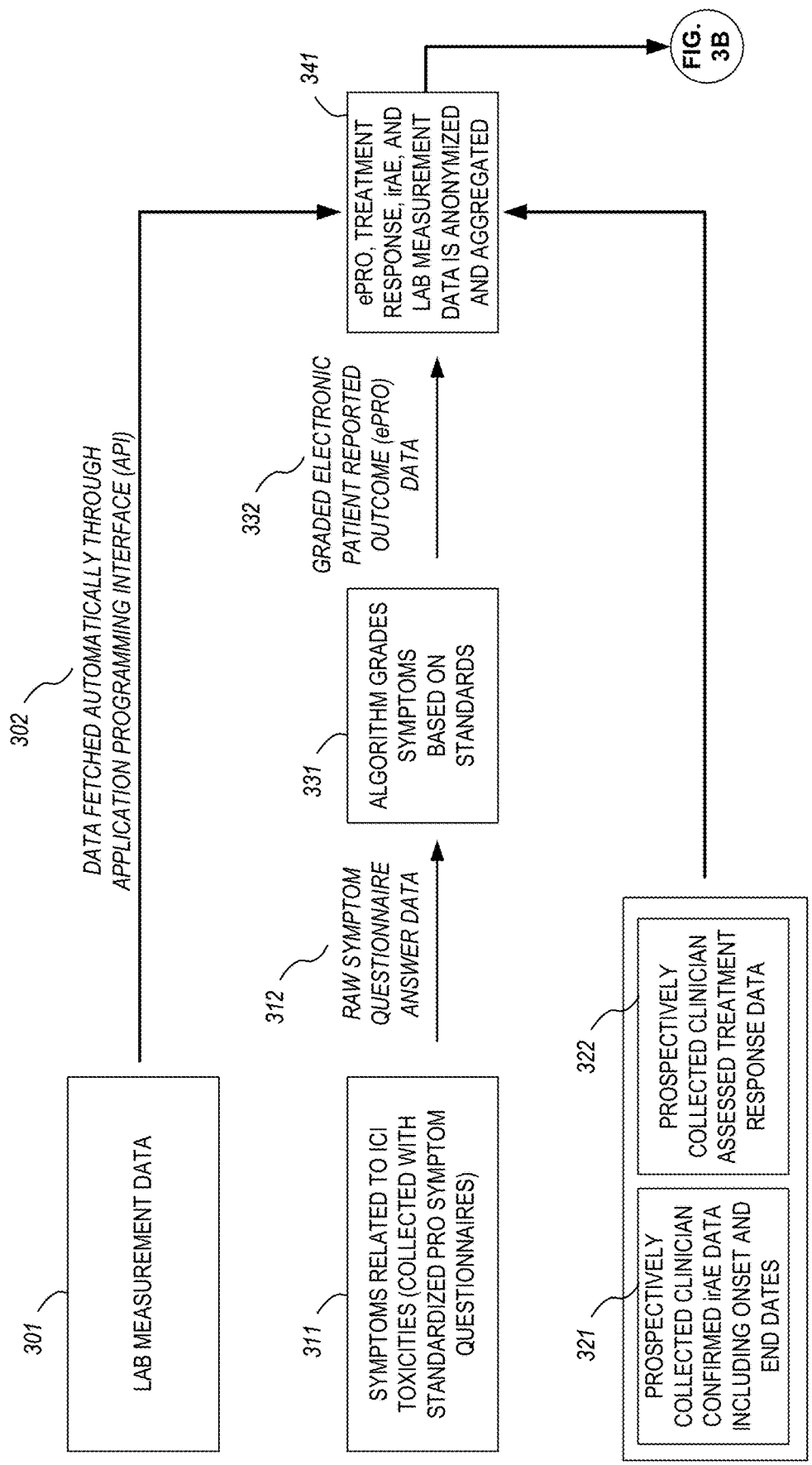
FIGS. 3A-3B illustrate a flowchart of a data modeling framework for predicting objective response rate with use of immune checkpoint inhibitor therapies, according to some examples.
Figure 3B:
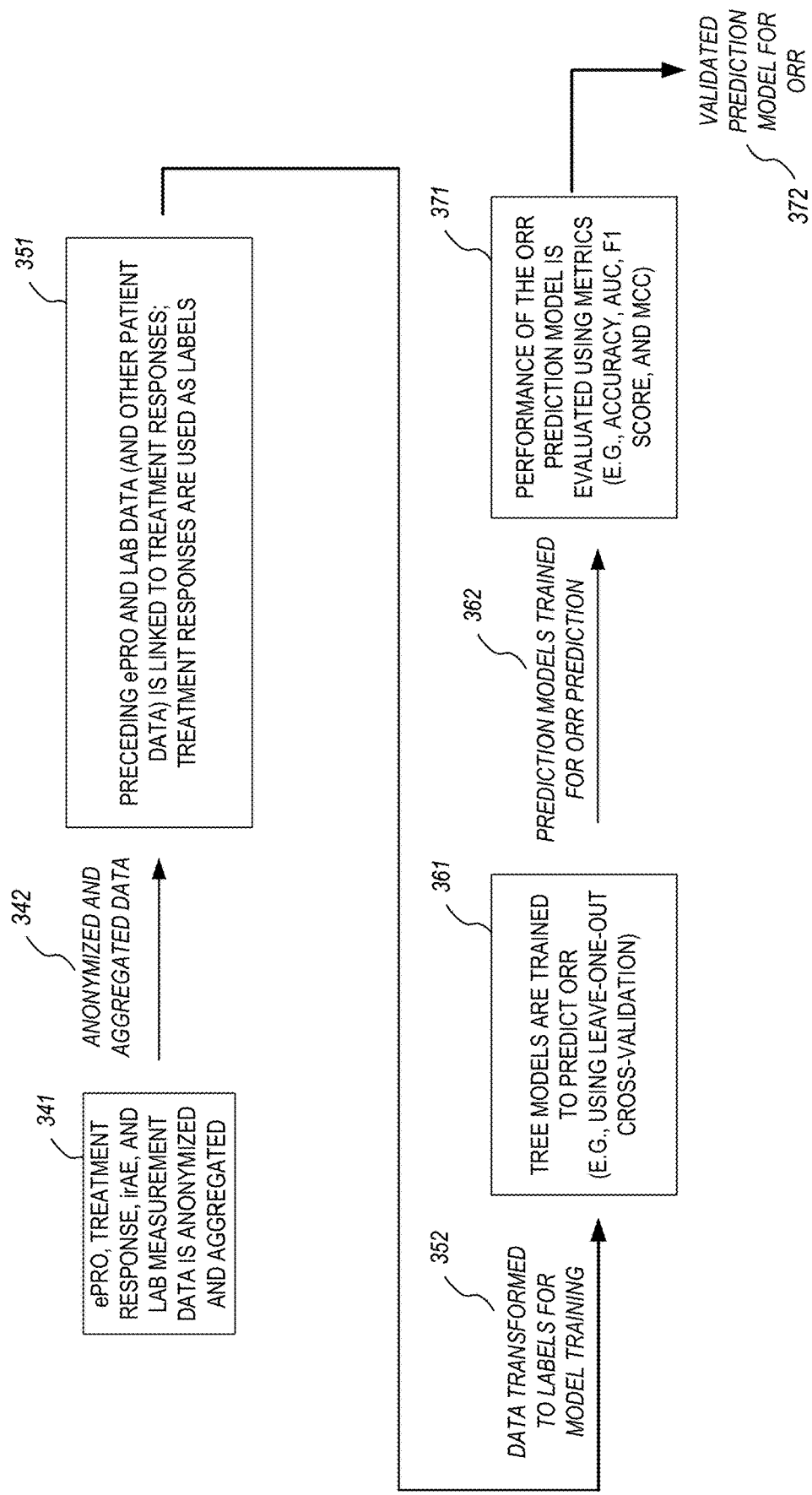

The complete modeling framework for predicting ORRs is detailed in the flowchart of FIGS. 3A-3B. Here, similar to the approach discussed with reference to FIGS. 2A-2B, data is collected and used for training specific types of prediction models.

The flowchart begins in the example of FIG. 3A with the collection or receipt of three data sets: lab measurement data 301 collected from patients undergoing therapy (or therapies); symptom data 311 related to the therapy (or therapies) that has been collected with standardized symptom questionnaires; and treatment data including prospectively collected (and clinician confirmed) adverse events data 321 (including onset and end dates) and prospectively collected clinician-assessed treatment response data 321. In an example, the lab measurement data 301 is collected from patients undergoing ICI therapies, and is the same group that reported symptoms in symptom data 311 and is associated with the irAE data for the adverse event data 321 and the treatment response data 322. Also in an example, the questionnaires used to collect the symptom data 311 is based on the user interfaces and functions described with reference to FIGS. 1A to 1F. In the example of ICI therapies, such standardized PRO symptom questionnaires can be used to collect symptoms specifically related to ICI toxicities.

The data 301, 311, 321, 322 can be provided, obtained, retrieved, or stored with various technical mechanisms. This may include, automatically retrieved lab measurement data 302 that is obtained through an application programming interface; and the retrieval of the adverse event data 321 and the treatment response data 322, which are compliant with some standardized metric or standard such as CTCAE (for adverse events) and RECIST (for treatment responses).

Additional processing may be used to convert raw symptom questionnaire answer data 312 into graded electronic patient reported outcome (ePRO) data 332, such as with the use of an algorithm that grades individual symptoms of the raw data 312. Such grading may be based on some standardized metric or standard (such as international standards relevant to the condition or treatment). Ultimately, the results of the data, collected as ePRO data, treatment response data, irAE data, and lab measurement data, is anonymized and aggregated with various data functions 341 into an anonymized and aggregated data set 342.

Continuing with the flowchart of FIG. 3B, the anonymized and aggregated data set 342 can be additionally processed with a linking function 351. Here, the preceding ePRO data and lab measurements, both as changes from the baseline values, are linked to the treatment responses. Also, patient age, sex, weeks from treatment initiation, and irAE presence (e.g., is irAE ongoing during treatment response assessment) are linked to the treatment responses. Treatment responses are used as labels. This produces a labeled data set 352, providing labels for model training.

The labeled data set 352 is further processed at a training function 361, where the model algorithm (e.g., Extreme Gradient Boosting (XGBoost) tree models) are trained to predict ORR, such as with use of a leave-one-out cross-validation (LOOCV). Such training may produce multiple models, each time iteratively leaving one sample out as a test set. This produces multiple prediction models 362 trained for ORR prediction.

The performance of the multiple prediction models 362 may be evaluated with an evaluation function 371, which evaluates the performance of the model using the evaluation metrics. The evaluation metrics may include those discussed above in TABLE 1. This produces a validated prediction model 372, specifically trained and validated to predict ORR for a particular oncology treatment.

In an example, treatment responses according to RECIST 1.1 are divided into binary categories, i.e. objective response (PR+CR) vs no objective response (SD+PD). The binary categories can predict the following:
  (a) Complete response (CR) or partial response (PR), i.e. patient has an objective response.
  (b) Stable disease (SD) or progressive disease (PD), i.e. patient does not have an objective response.

Prediction performance of the model for unseen samples can be evaluated using leave-one-out cross-validation (LOOCV), which trained and tested multiple models, each time iteratively leaving one sample out as a test set. The LOOCV prediction performance can be evaluated with accuracy, AUC (Area Under Curve), F1 score and MCC (Matthew's correlation coefficient). These performance metrics are discussed above in TABLE 1.

Figure 4:
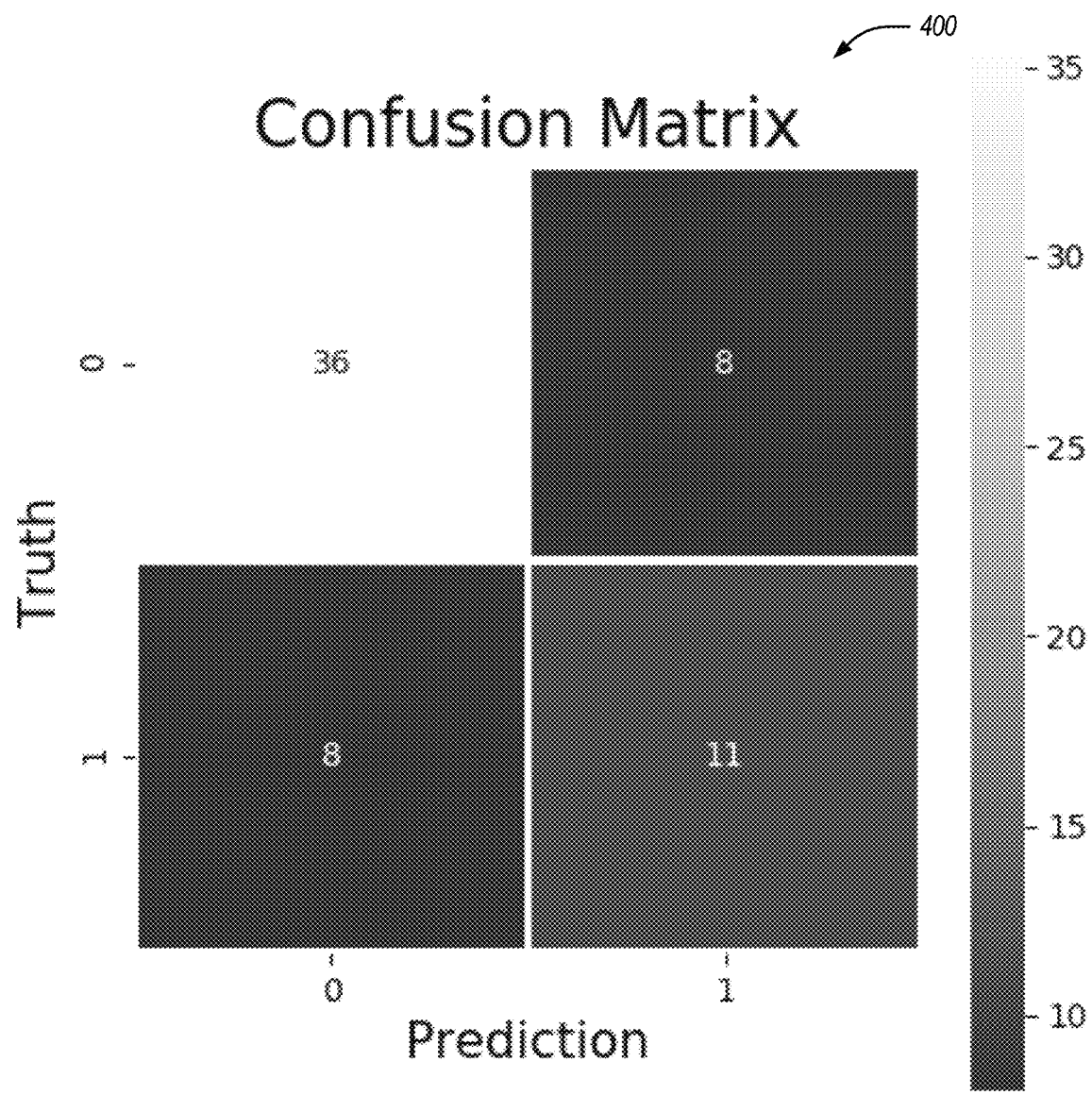
FIG. 4 illustrates a confusion matrix provided from a combination of leave-one-out cross-validation predictions for predicting objective response rate in immune checkpoint inhibitor therapies, according to some examples.

In an example, an ORR prediction model provides a suitable LOOCV performance with all four metrics of TABLE 1. FIG. 4 presents a confusion matrix demonstrating the results of combining all LOOCV predictions, and FIG. 5 illustrates feature importances from an example model implementation that is trained with all available samples.

FIG. 4 specifically illustrates a confusion matrix 400 for predicted ORR of an example implementation. The upper left corner of matrix 400 shows correctly classified negative, lower right corner correctly classified positive, upper right corner false positive and lower left corner false negative samples. Negative samples consist of SD and PD responses and positive samples CR and PR responses.

Figure 5:
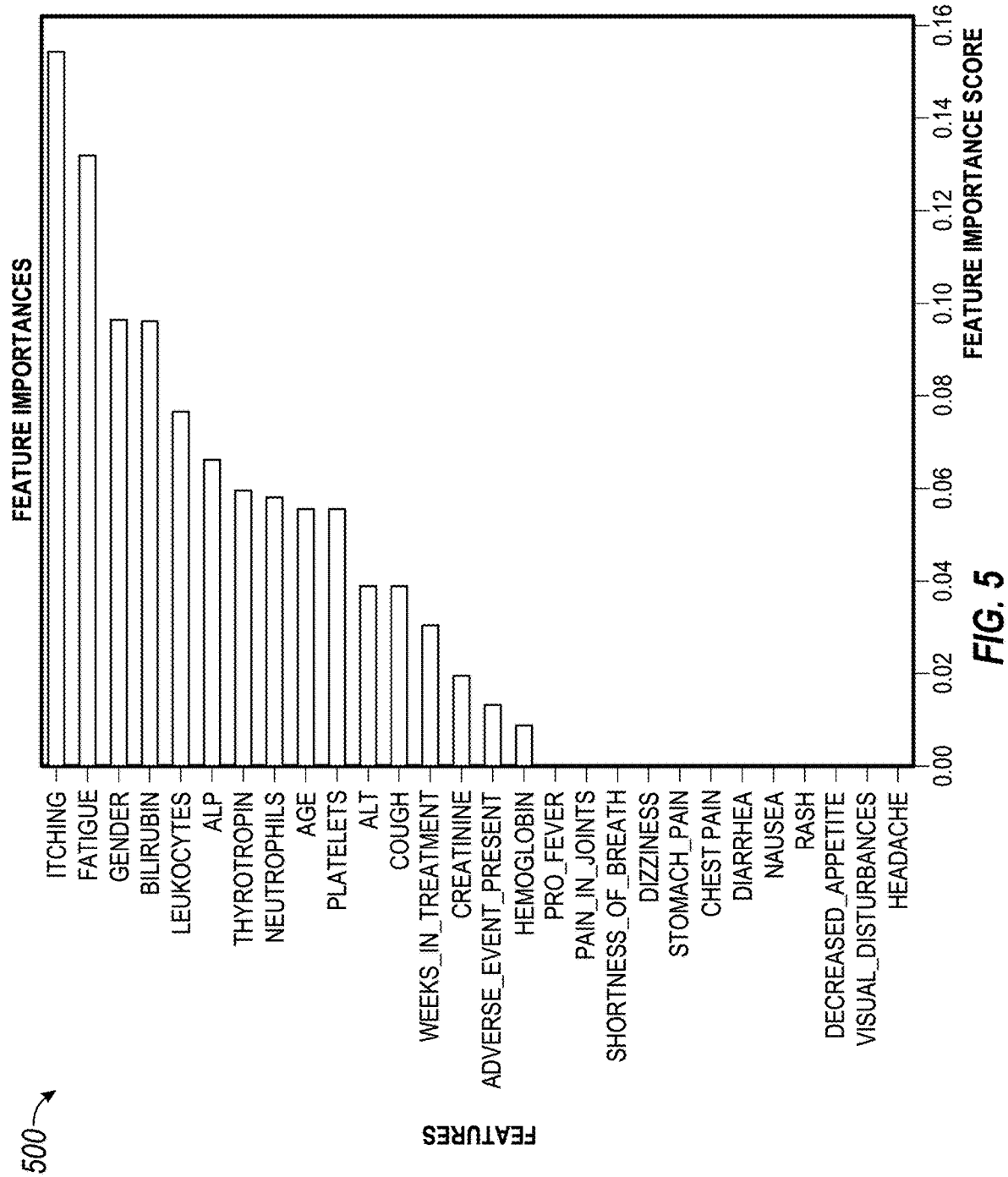
FIG. 5 illustrates feature importances from a model trained for predicting objective response rate in immune checkpoint inhibitor therapies, according to some examples.

FIG. 5 specifically illustrates the feature importances of an example implementation of an ORR prediction model, trained with all available samples. The displayed importances depict the relative average improvement in prediction accuracy across all trees in the model where a certain feature is utilized. The importances should be considered as relative to each other.

It will be understood that ML models built using ePRO symptom data and other clinical data can be used in treatment response prediction even with a limited size cohort. AI models thus offer a change for individually evolving follow-up with a possibility for prediction of important clinical events such as therapy toxicities and/or benefits.

Machine Learning (ML) for Predicting Patient-Reported Symptoms During Radiotherapy (RT)

As noted above, electronic collection of ePROs as part of routine clinical care can provide insights on patient experience for cancer therapies. Such insights may be extended during and after radiotherapy treatment. In particular, the following explains the feasibility of using ML to predict the occurrence and severity of radiotherapy-related symptoms from ePROs collected from breast and prostate cancer patients. Prediction of radiotherapy-related symptoms could enable earlier interventions, and hence, improved treatment safety and better quality of life for the patients.

For example, consider an example patient population consisting of breast and prostate cancer patients who had reported their symptoms through a software application (e.g., in an user interface similar to FIG. 1A) as part of their radiotherapy monitoring. The symptoms can be reported and graded based on the CTCAE system and the patient groups were analyzed retrospectively. Specifically, such data may be provided from example breast and prostate cancer datasets.

Occurrence and severity of monitored RT-related symptoms can be predicted using gradient boosting, a ML algorithm. The algorithm can be implemented with an open-source Python library XGBoost. XGBoost is an ensemble of CARTs (classification and regression trees) where several weak learners (CARTs) are combined to form a strong learner in an iterative manner by adding more trees to the previous model to improve the classification performance. XGBoost models are able to provide confidence scores (probabilities) for the predictions as an output.

Using supervised learning, the models are trained to predict the occurrence and severity of symptoms during the next week based on the data from three previous ePRO reports, as well as the age of the patient and the time from the treatment initiation. For both breast and prostate cancer datasets, the model training and hyperparameter tuning can be conducted using a training dataset, e.g., including 70% of the data. In the rest of the datasets some fraction of the data (e.g., 30% of the data) were excluded from the model training. These test datasets can be reserved solely for the performance evaluation of the trained models to give an approximation of the prediction performance in real life settings.

Figure 6:
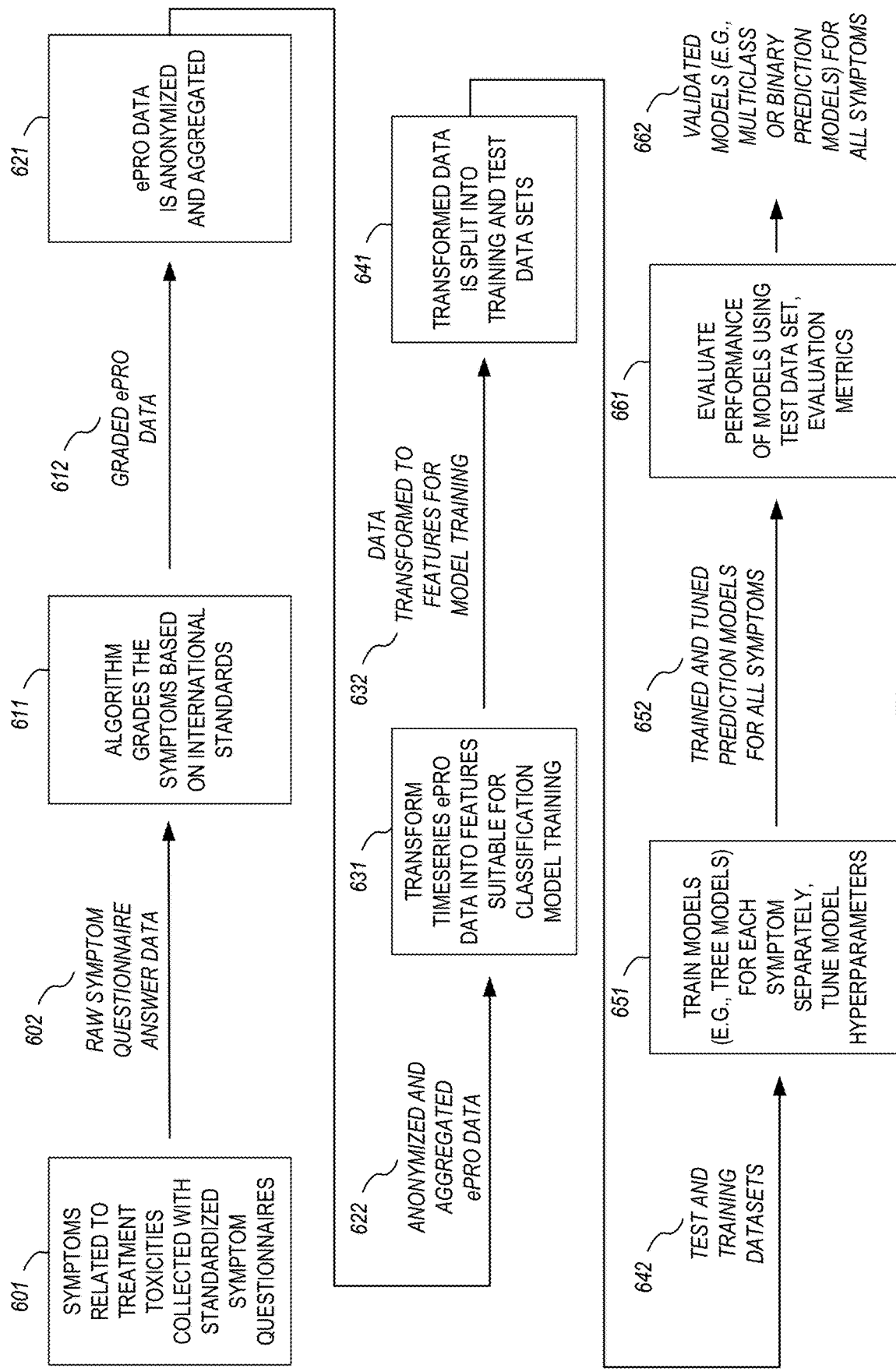
FIG. 6 illustrates a flowchart of a data modeling framework for determining the relevance of treatment toxicity related symptom occurrence and severity prediction in connection with radiation therapy, according to some examples.

The complete modelling framework for this technique is presented in FIG. 6. This framework indicates the relevance of treatment toxicity related symptom occurrence and severity prediction models.

Specifically, FIG. 6 illustrates a flowchart of a data modeling framework for determining the relevance of treatment toxicity related symptom occurrence and severity prediction in connection with radiation therapy. The flowchart begins with the collection of symptoms 601, such as those symptoms related to treatment toxicities collected with standardized symptom questionnaires (e.g., depicted in FIGS. 1A to 1F). This produces a raw symptom questionnaire answer data set 602. Similar to the flowcharts depicted in FIGS. 2A to 3B, such raw data can be assessed by a grading function 611, such as an algorithm that grades the symptoms based on international standards, to produce graded ePRO data 612. This ePRO data may be anonymized and aggregated with function 621, to produce anonymized and aggregated data set 622.

A transformation function 631 is applied to transform the time series of ePRO data into features suitable for classification model training. The transformed data 632 represents the results of such data, which has been transformed to features for model training. A further data processing function 641 serves to split the transformed data into training and test data sets 642.

The training and test data sets 642 can be used at a training function 651. The training function 651 may operate to train models (e.g., multiclass or binary XGBoost tree models) for each symptom separately, using the training data set. Additionally, the model hyperparameters may be tuned using repeated stratified five-fold cross-validation. This produces a set of trained and turned prediction models 652 for all symptoms.

Additional processing may occur to evaluate the performance of the models with evaluation function 661. This may include the evaluation of the models using the test data set, with evaluation metrics including accuracy and MCC for both binary and multiclass models. Finally, a set of validated models 662, such as multiclass or binary prediction models, are produced for all symptoms.

In an example, three symptom severities, following the CTCAE system, can be predicted, if feasible with respect to the data. In this case the predicted classes, may include, for instance, predicted symptom grades as 0 (no symptom), 1 (mild) or 2-3 (moderate or severe). Grades 2 and 3 can be combined if there is low prevalence of the severe grades in the datasets. These cases can be considered as multiclass classification problems, as there were three classes to be predicted.

For some symptoms, the prevalence of the higher severity grades may be very low, some of the grades were not reported at all in the dataset, or the grading algorithm did not produce all grades between 0 and 3. For these symptoms, only the occurrence of the symptom was predicted, i.e., the predicted classes were either grade 0 or grade 1-3. These cases can be considered as binary classification problems.

As noted, the prediction performance of the trained ML models can be evaluated using the test datasets, by using accuracy and Matthew's correlation coefficient (MCC). For the multiclass classification cases (three severity grades), the multiclass versions of accuracy and MCC can be used. MCC summarizes all possible cases for binary or multiclass predictions: true and false positives and true and false negatives. It is suitable for analyzing imbalanced datasets, where one class is rarer than the other or others. MCC returns values between −1 and 1 where 0 indicates random classification, 1 perfect classification and −1 a completely contradictory classification. Numerical values of MCC as 0.30 to 0.39, 0.40 to 0.69, and 0.70 or higher refer to moderate, strong, and very strong positive correlation, respectively. For some symptoms, predictions can be binary, i.e., symptom present (grades 1-3) or symptom not present (grade 0); for others, three severity classes can be predicted.

Figure 7B:
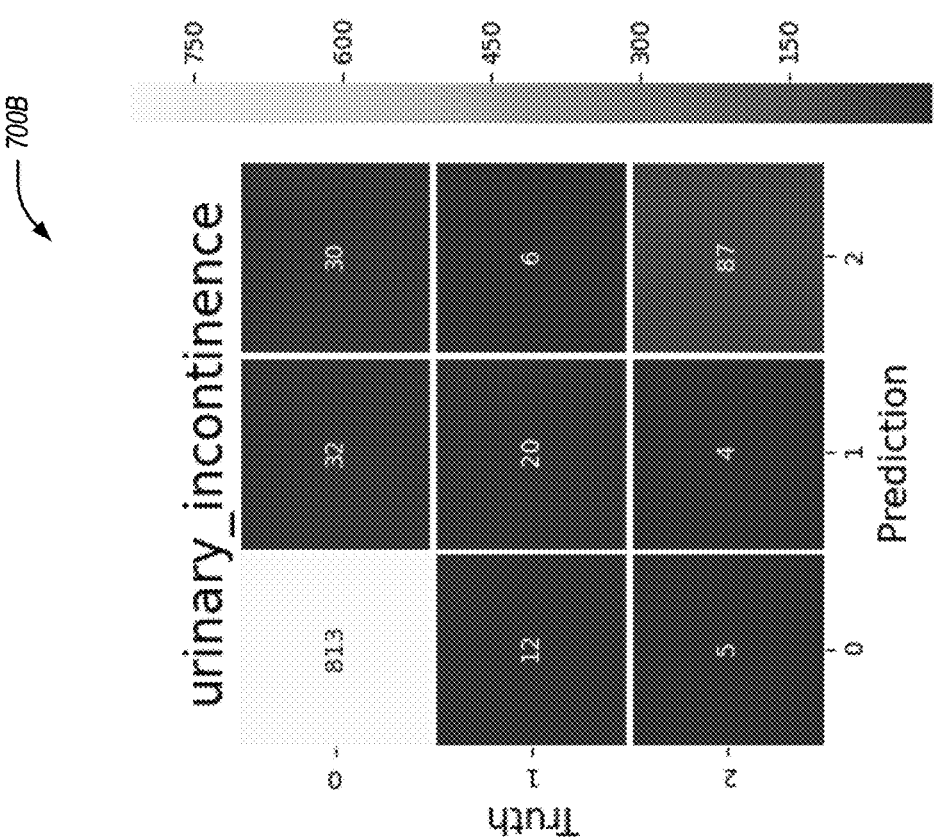
FIGS. 7A and 7B illustrate confusion matrixes from a symptom severity prediction model for predicting symptom occurrence and severity prediction in connection with breast cancer and prostate cancer radiation therapy, according to some examples.
Figure 7A:
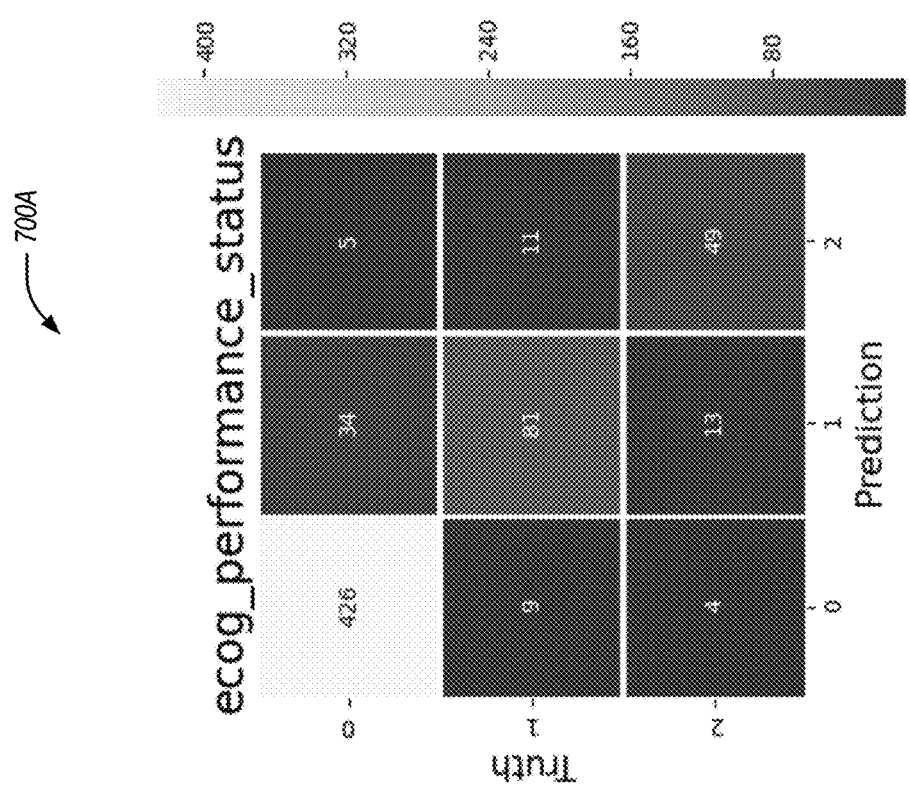

FIG. 7A illustrates a confusion matrix for a symptom severity prediction model for "ECOG performance status" with an example breast cancer test dataset, and FIG. 7B presents the same for "urinary incontinence" with an example prostate cancer test dataset. These two symptoms are presented as examples. It is visible from these figures that the false negatives, i.e., cases where the predicted grade is too low (3 squares in lower left triangle) are less common than the false positives, i.e., cases where the predicted grade is too high (3 squares in upper right triangle).

Figure 8A:
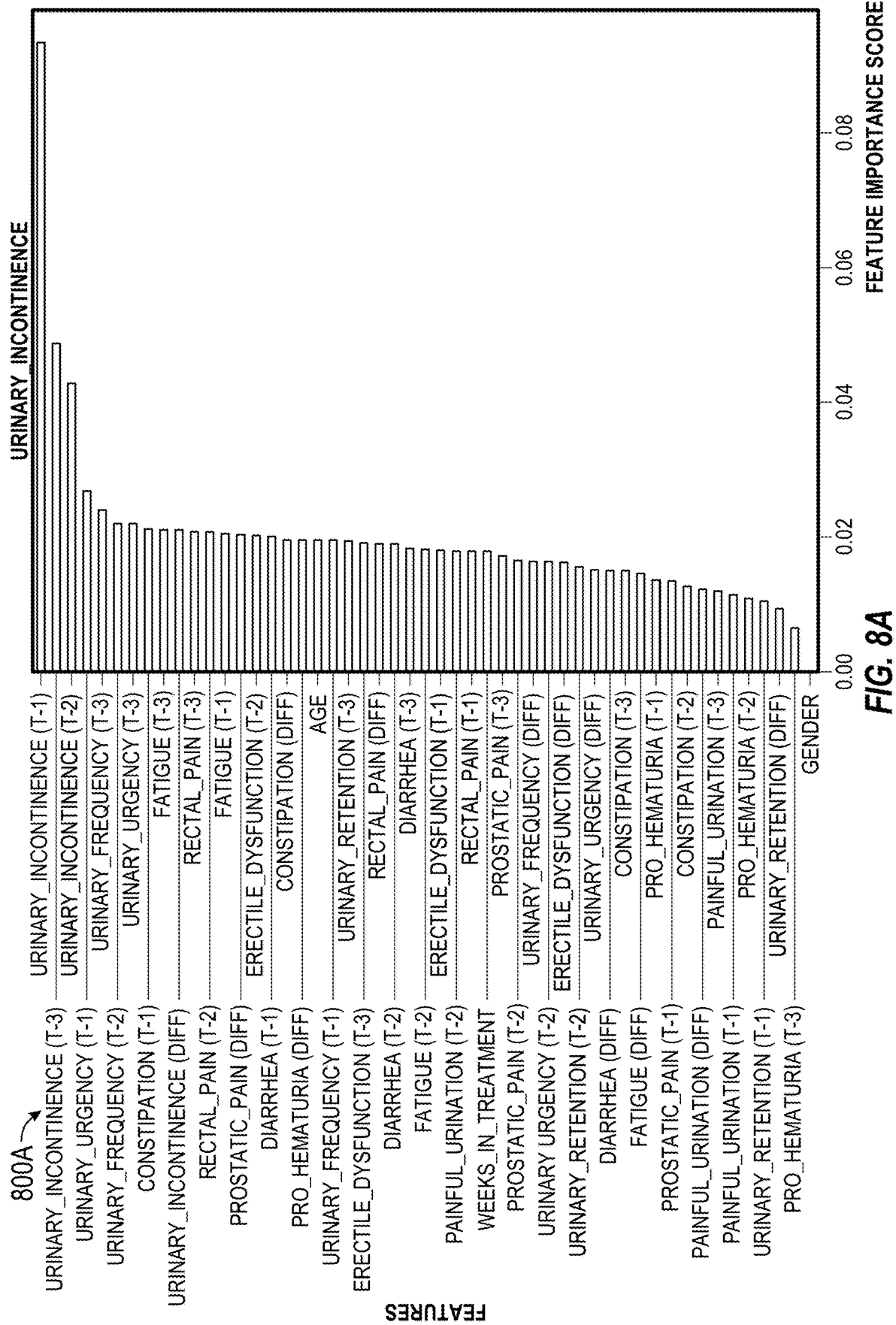
FIGS. 8A and 8B illustrate feature importances from symptom severity prediction models for predicting symptom occurrence and severity prediction, according to some examples.
Figure 8B:
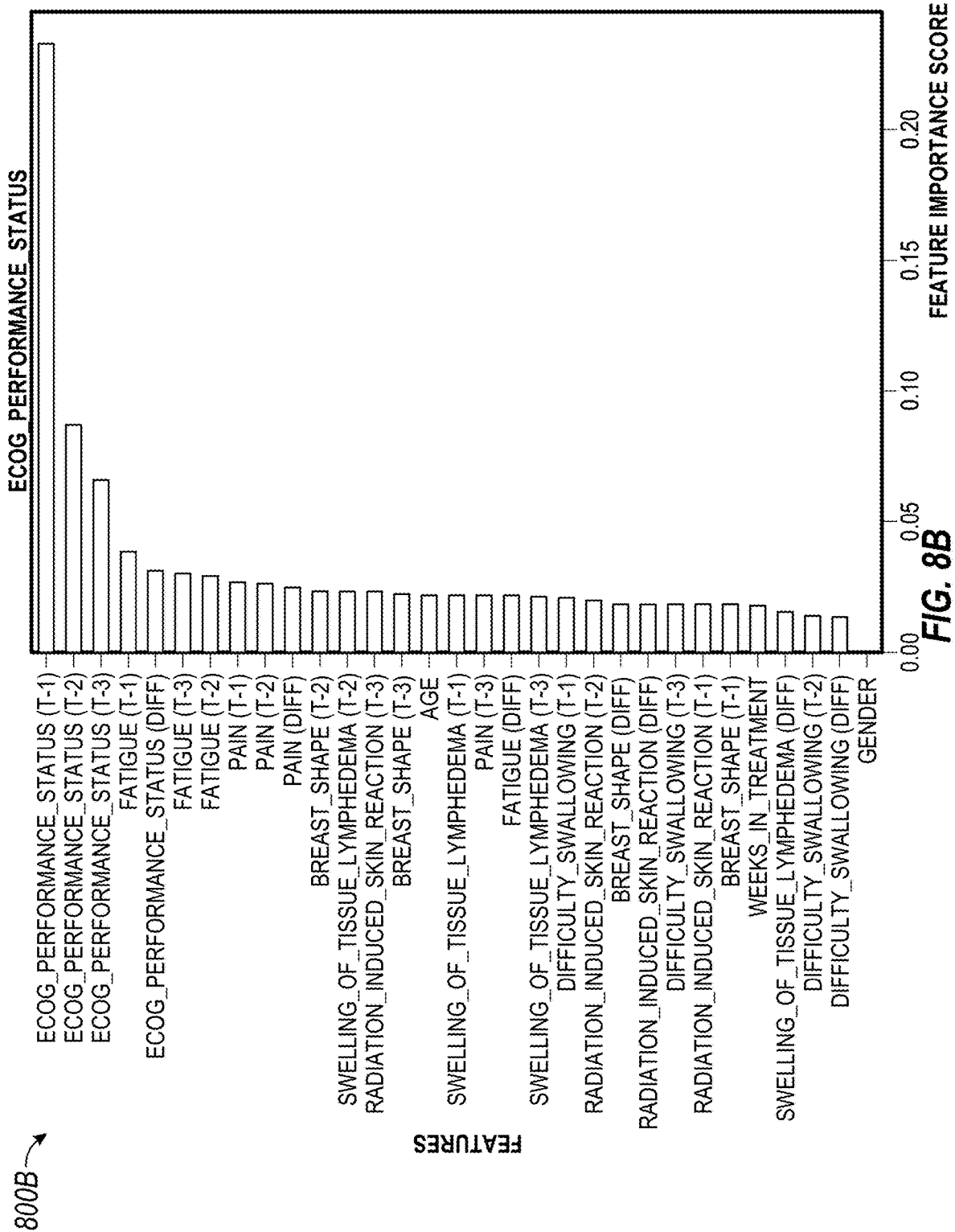

FIG. 8A illustrates a feature importances for a "ECOG performance status" symptom severity prediction model, and FIG. 8B illustrates the feature importances for a "urinary incontinence" symptom severity prediction model. FIG. 8A shows that the most important features were previous values of "ECOG performance status", "fatigue" and "pain". In FIG. 8B, the most important features were the previously reported values of three urinary symptoms including "urinary incontinence", "urinary urgency" and "urinary frequency". The displayed importances depict the relative average improvement in prediction accuracy across all trees in the ensemble model where a certain feature is utilized. The importances should be considered as relative to each other. This data analysis suggests that the severity (divided in three severity groups) of patient reported symptoms during the upcoming week can be predicted with good to excellent accuracy for most symptoms both for breast and prostate cancer patients undergoing RT, using only ePRO data and basic information (age and time in treatment) as inputs.

Prediction models could be further improved by adding more data sources including laboratory values and information about potential adverse events, the stage of cancer, and the radiotherapy related data. With these additions, it might be possible to predict the treatment related adverse events and not only the patient reported symptoms related to the treatment related adverse events.

For instance, the presented symptom occurrence and severity prediction models could be used for enabling earlier interventions for symptom progression and adverse events by providing predictive information for the care team. The presented symptom occurrence and severity prediction models could also be used for providing proactive and personalized guidance and support for the patients based on the predicted symptom progression. This may also enable more precise and timelier follow-up by timing additional symptom questionnaires based on the predicted symptom progression.

Performance metrics for prediction models may be calculated for the onset and continuity of symptoms related to adverse events from radiotherapy for specific radiotherapy treatments such as for breast cancer. Such performance metrics may be calculated during treatment (e.g., in connection with acute toxicities) and after treatment (e.g., in connection with late toxicities). Relevant performance metrics may include those discussed with reference to TABLE 1.

Figure 9:
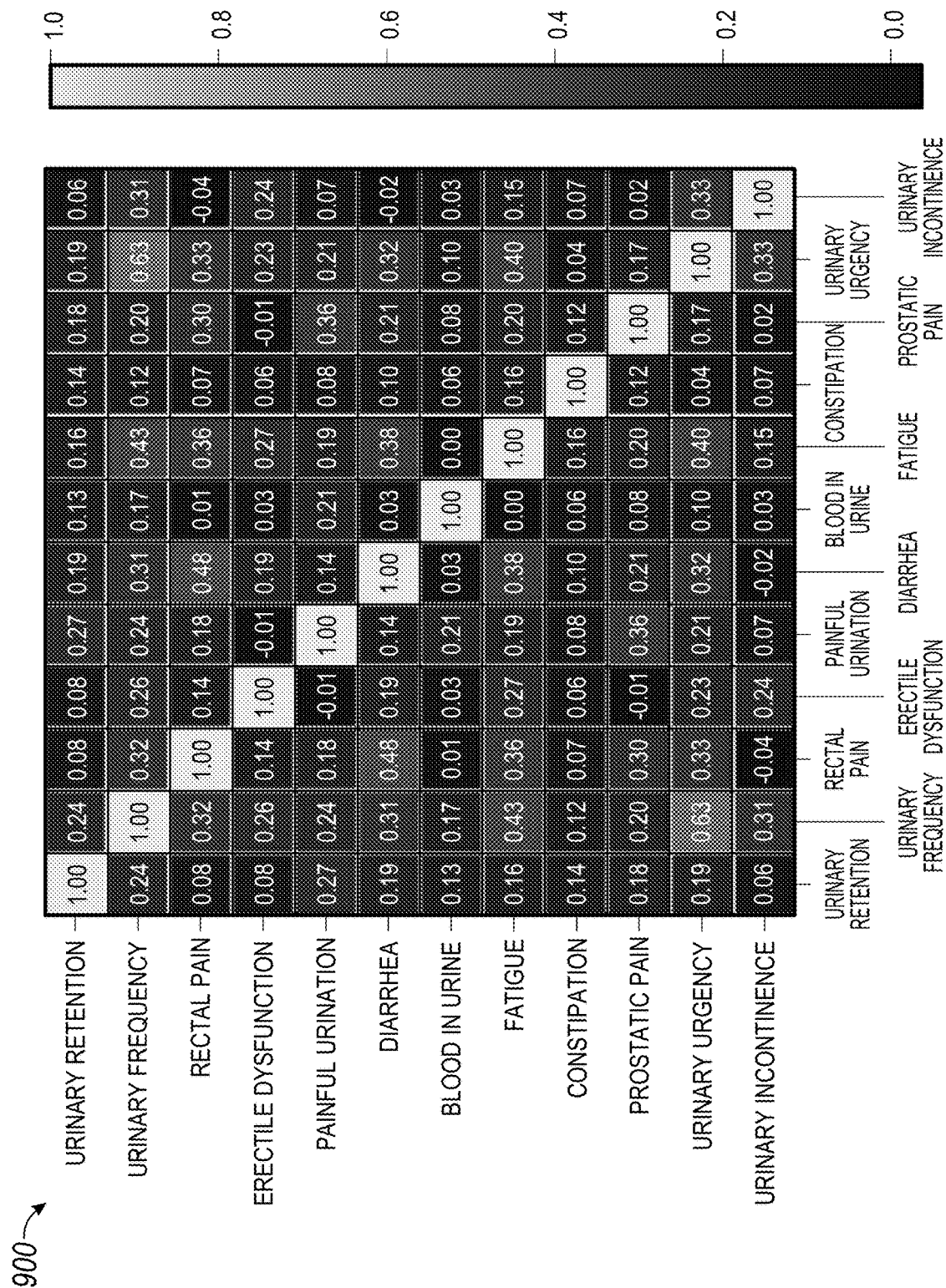
FIG. 9 illustrates predicted toxicity profiles provided in connection with prostate cancer radiotherapy, according to some examples.

As another example of predicting toxicities from radiotherapy, FIG. 9 depicts a predicted toxicity profile 900, provided in connection with prostate cancer radiotherapy. Specifically, this profile 900 depicts correlations between predictors when using 1 lagged variable. Other correlations between predictors may exist using 2 lagged variables, 3 lagged variables, 3 lagged variables and differences, or other variations.

Broader Applications of Modeling Framework for Radiotherapy Planning and Treatment Utilizing the same modeling framework, a variety of correlations may be identified between patient-reported symptoms after external beam radiotherapy. One such use includes personalizing the symptom management experience based on symptom clustering and predictive models. Another such use includes educating patients, to provide information for taking right actions in a more timely manner during and after a radiotherapy treatment course. Another such use includes predicting toxicities from radiotherapy for health care providers (HCPs) to enable earlier interventions to symptoms. Other uses of machine learning-based predictive models may be integrated into a digital health platform.

Thus, the goal is for catching possible RT-related toxicities earlier through personalized symptom tracking and patient education, and predicting toxicity profile, to enable HCP management of adverse events as timely as possible and assist with optimizing upcoming fractions (i.e. Adaptive RT). Ultimately this will result in improved quality of treatment for patients.

FIG. 10A depicts a graphical report 1000A with a result of predicting a toxicity profile. Here, a variety of time-charted symptoms 1021 are indicated based on a respective week timeline 1011. The toxicity profile provides a predicted estimation 1031 for a future week, including probabilities for each classified symptom.

Figure 10B:
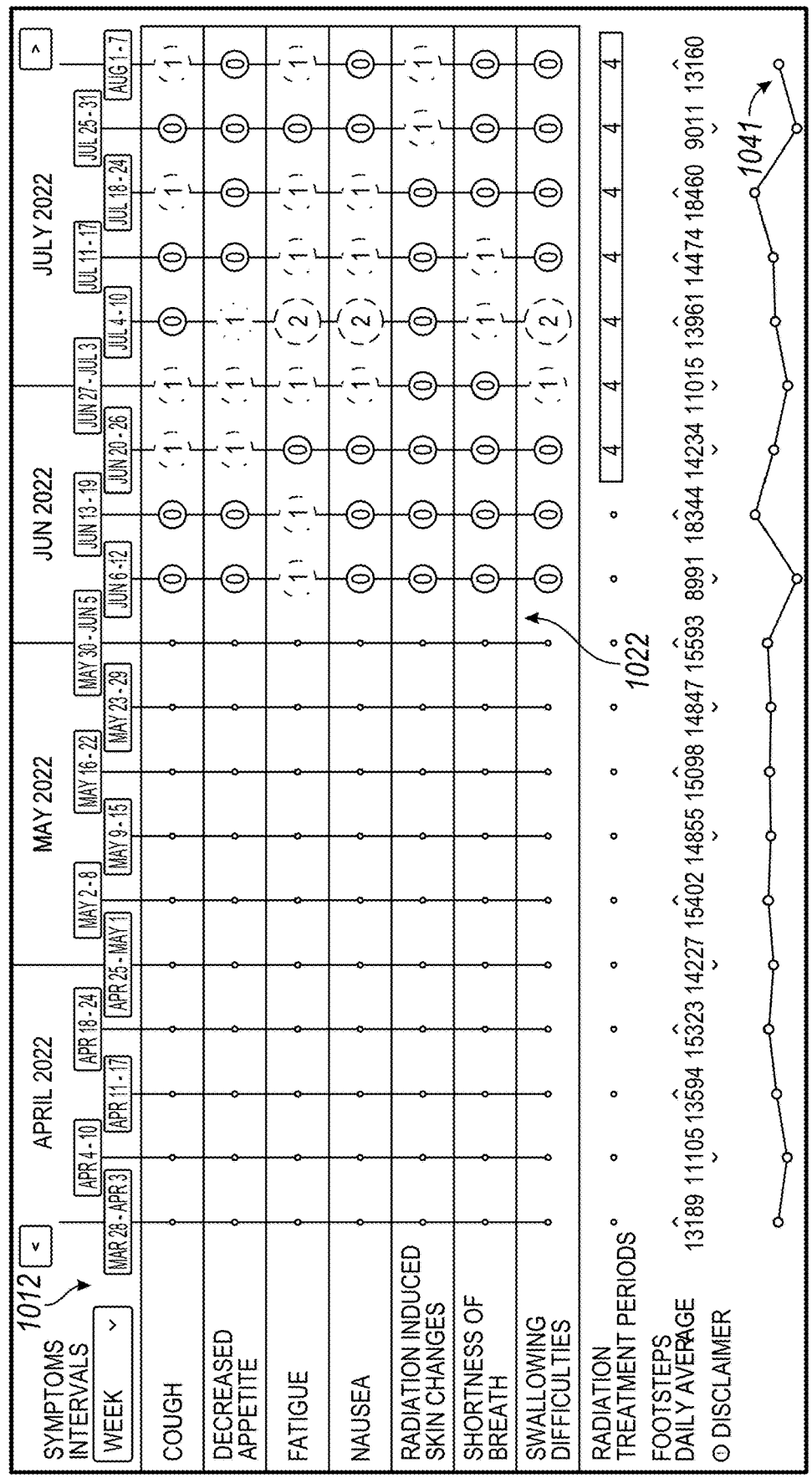

Similarly, FIG. 10B depicts a graphical report 1000B with a result of predicting a second toxicity profile. Here, the time-charted symptoms 1022 for radiotherapy are indicated based on the timeline 1012, with different numbers, colors, and sizes of indicates used to indicate severity or number of adverse events. The toxicity profile can also provide a predicted estimation for a future week (not shown), including probabilities for each classified symptom. Additionally, a graphical comparison 1041 can be provided relative to some other data source, such as patient data (steps) over the time period as measured by a wearable device.

Figure 11:
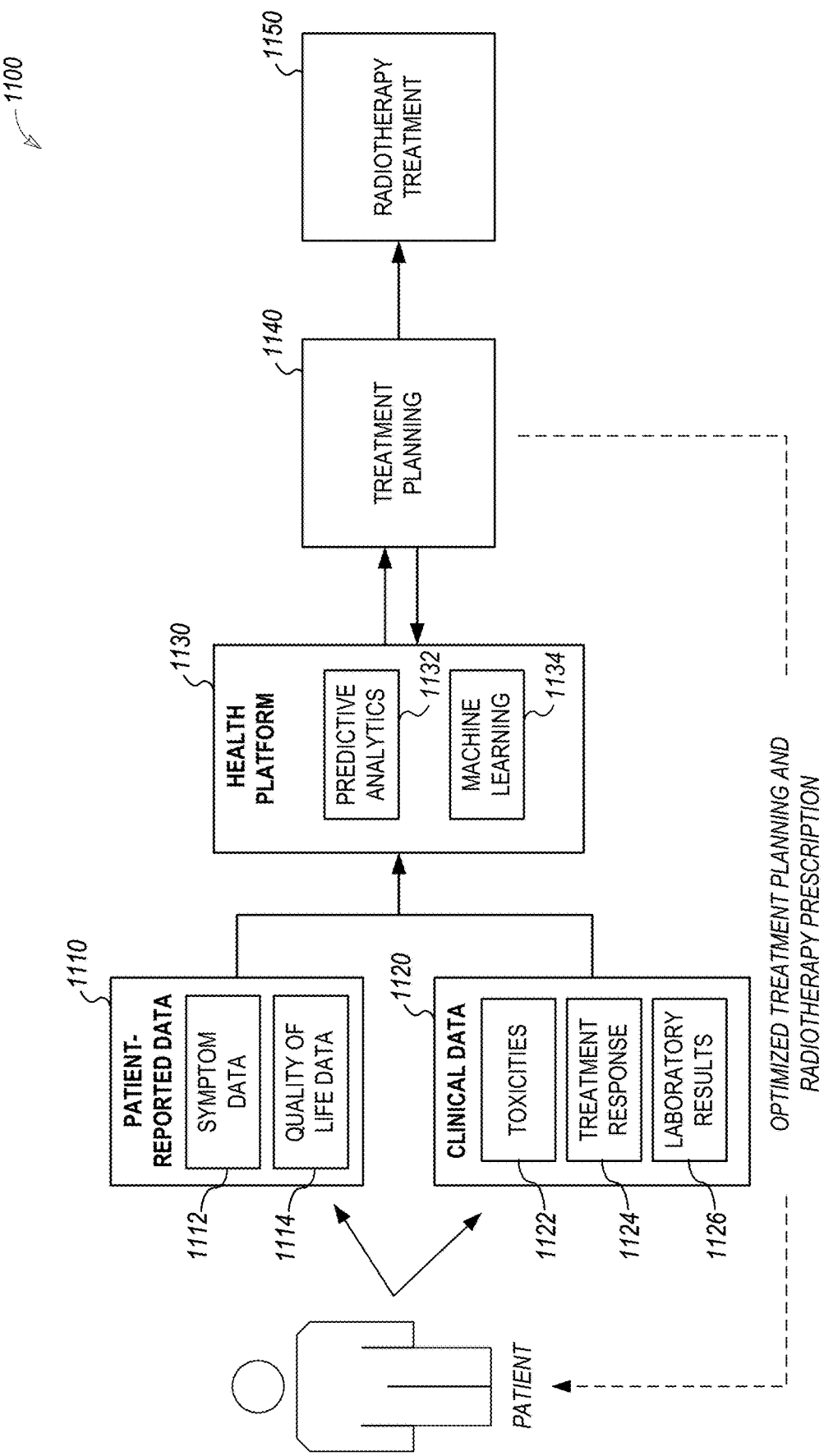
FIG. 11 illustrates a workflow for an optimized radiotherapy treatment planning process, according to some examples.

FIG. 11 depicts a workflow for an example optimized radiotherapy treatment planning process. Here, this planning process enables changes and modifications based on predictive analytics and machine learning in order to enable adaptive radiotherapy.

As shown, various aspects of optimized treatment planning 1140 and radiotherapy prescription 1150 may be generated based on combining patient-reported outcomes data 1110 (e.g., symptom data, quality of life data) with clinical data 1120 (e.g., toxicities, treatment response, laboratory results), which are analyzed by predictive analytics 1132 and machine learning 1134 in a health platform.

Other data and analytical processes may also be employed in this workflow. Although only one model is shown, it will be understood that a separate model may be used and trained for each symptom (e.g., using a different model for each prediction, with as many models as tracked symptoms).

Figure 12:
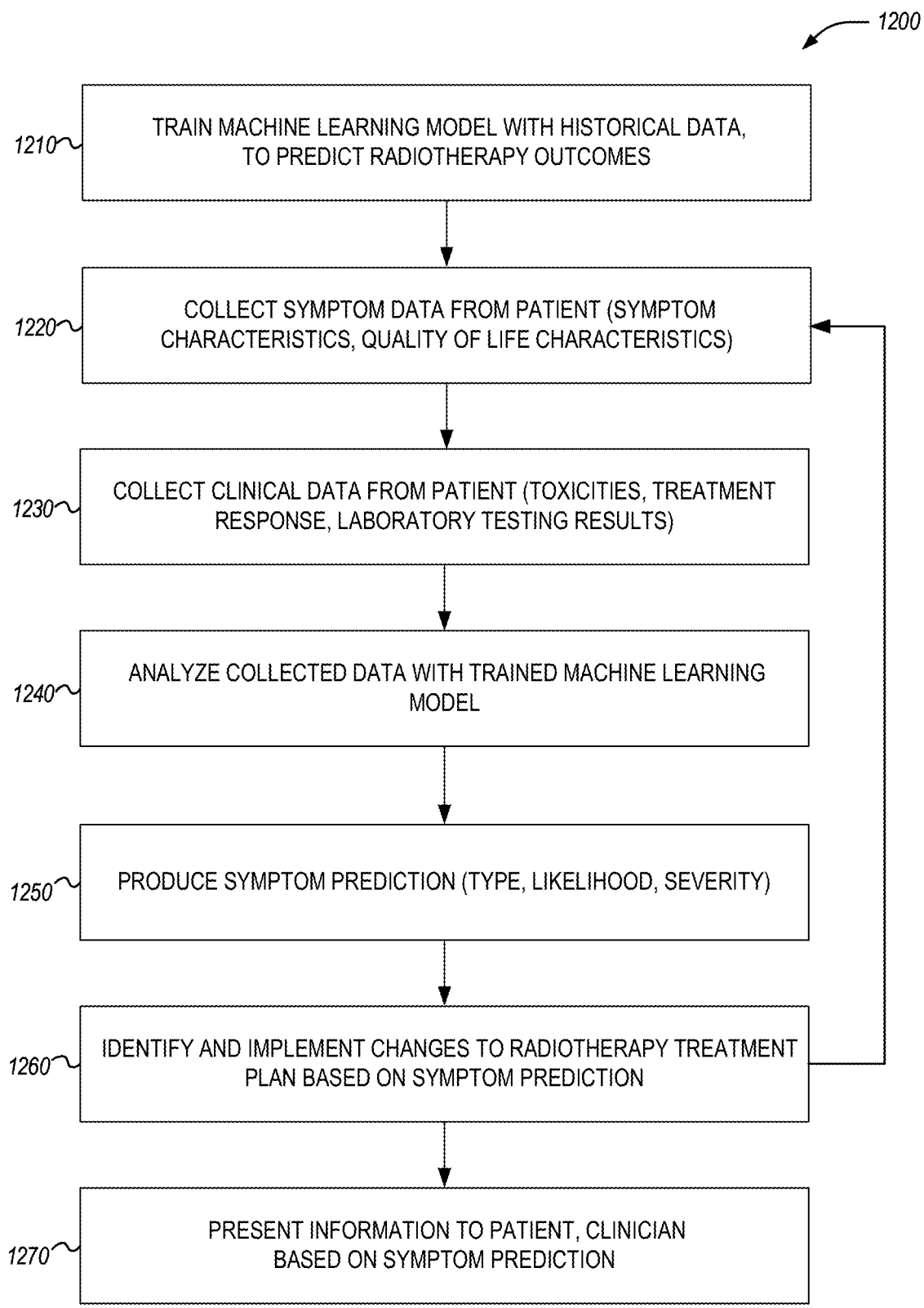
FIG. 12 illustrates a flowchart for a method of optimized radiotherapy treatment planning, according to some examples.

FIG. 12 illustrates a flowchart 1200 for an example method of optimized radiotherapy treatment planning.

The flowchart starts at operation 1210, to train a machine learning model with historical data, to predict radiotherapy outcomes. This may involve offline or online training as discussed herein.

At operation 1220, symptom data is collected from a particular patient (e.g., symptom characteristics, quality of life characteristics), and at operation 1230, clinical data is collected from the particular patient (e.g., toxicities, treatment response, laboratory testing results).

At operation 1240, the collected data is analyzed with the trained machine learning model, and other aspects of analytics.

At operation 1250, the machine learning model produces a symptom prediction, such as an analysis which produces a type, likelihood, and severity of symptoms.

At operation 1260, changes to a radiotherapy treatment may be identified and implemented, based on the symptom prediction. This may occur in an adaptive workflow, with repeating of operations 1220-1260 for current or subsequent treatments. Such changes may also be implemented with use of a feedback loop from a secondary system, to provide real-time adaptive radiotherapy treatment modifications.

At operation 1270, the flowchart 1200 concludes with the presentation of information to a patient or clinician, based on the symptom prediction.

A variety of improvements or adaptations may be used to extend the present techniques to other clinical or monitoring aspects. For example, the detection of rare (or common) adverse effects can be used to trigger other types of adaptive radiotherapy planning changes, warnings, or treatment indications. Because the predictive model may be run on an ongoing basis (e.g., each and every time the patient submits a set of responses to a symptom questionnaire), any emerging adverse effects can be quickly identified and responded to.

In a similar manner, the present techniques may be used to handle late emerging symptoms, or identify outcomes of specific doses or characteristics. In this manner, outcome data could be used as input for helping developing or selecting an optimal plan, including identifying least negative plans (minimizing symptoms or adverse effects).

Figure 13:
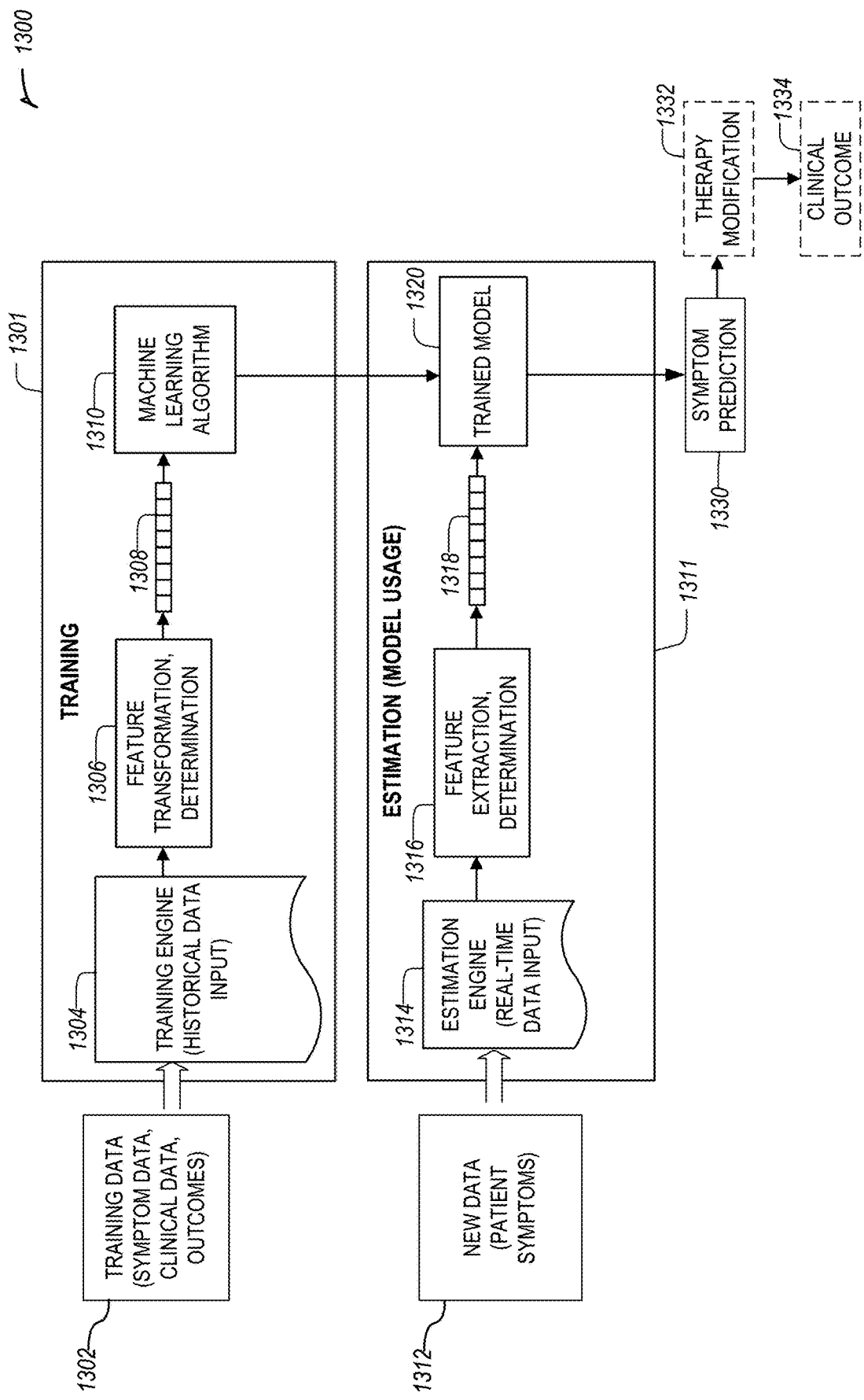
FIG. 13 illustrates a machine learning workflow for use in estimating patient symptoms in connection with a medical treatment, according to some examples.

Overview of Uses of Machine Learning and Implementing Computer Architectures for Oncology Treatment Workflows FIG. 13 illustrates a machine learning workflow 1300 for use in estimating patient symptoms in connection with a medical treatment. The machine learning workflow 1300 includes a training workflow 1301 and an estimation workflow 1311 to perform training (e.g., model training) and estimation (e.g., model inference or classification) operations, respectively. The workflow 1300 provides another view of data processing occurring with the training and treatment aspects discussed above.

In the training workflow 1301, training engine 1304 generates training inputs from transformed data (e.g., anonymized version of symptom data, clinical data, outcome data 1302), to produce features 1308 for training. Feature transformation and determination 1306 identifies relevant features 1308 from the data input, which are used to produce a machine learning algorithm 1310. The machine learning algorithm 1310 produces a trained model 1320 (e.g., a regression model) based upon the features 1308 and the correspondence between symptom data and outcomes.

In the estimation (model usage) workflow 1311, newly captured data 1312 (e.g., information captured from a new patient) may be input to the estimation engine 1314. The estimation engine 1314 operates to use a feature determination engine 1316 to extract and determine relevant features of the newly captured data 1312 that are relevant to a corresponding patient state. The feature determination engine 1316 produces features 1318, which are input into the trained model 1320. The training workflow 1301 may operate in an offline manner to train the model 1320, such that weights of the model 1320 are learned during training and fixed. Then, during the estimation workflow 1311, the features 1318 are input into the trained model 1320, which internally uses the fixed weights to produce the estimation results, such as a symptom prediction 1330. The estimation engine 1314, however, may be designed to operate in an online manner. It should be noted that the trained model 1320 may be periodically updated via additional training or user feedback (e.g., additional, changed, or removed measurements or patient states).

The machine learning algorithm 1310 may be selected from among many different potential supervised machine learning algorithms. Examples of supervised learning algorithms include artificial neural networks, Bayesian networks, instance-based learning, support vector machines, decision trees (e.g., Iterative Dichotomiser 3, C4.5, Classification and Regression Tree (CART), Chi-squared Automatic Interaction Detector (CHAID), and the like), random forests, linear classifiers, quadratic classifiers, k-nearest neighbor, linear regression, logistic regression, and hidden Markov models.

The machine learning algorithm 1310 trains the model 1320 as described herein, based on how symptoms correspond to particular outcomes. In an example, the machine learning algorithm 1310 implements a regression problem (e.g., linear, polynomial, regression trees, kernel density estimation, support vector regression, random forests implementations, or the like). The resulting training parameters define the regression model (a generator) as a correspondence motion model for the chosen machine learning algorithm.

Figure 14:
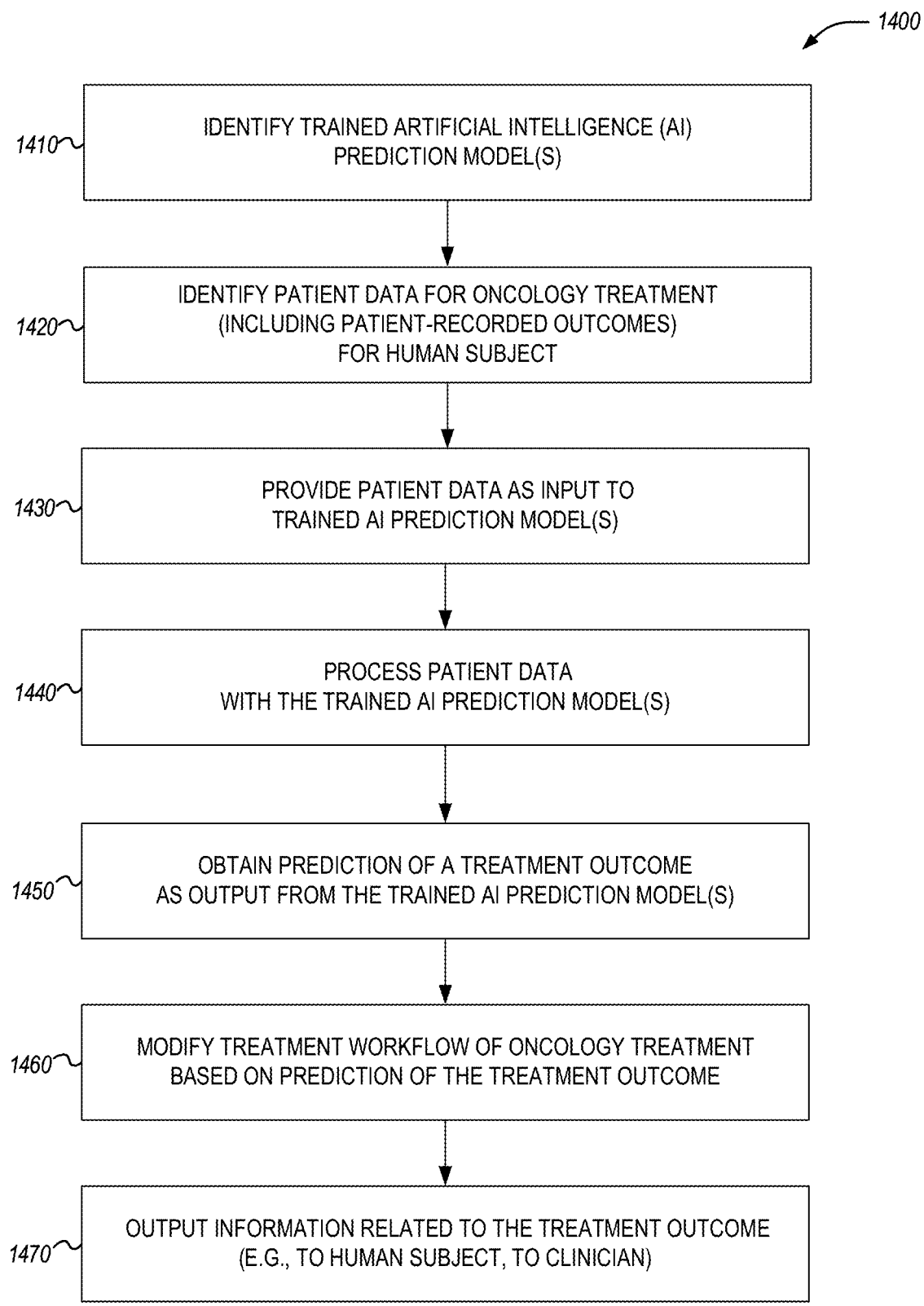
FIG. 14 illustrates a flowchart for a method of generating a predicted treatment outcome for an oncology treatment, according to some examples.

FIG. 14 illustrates a flowchart 1400 for an example method of generating a predicted treatment outcome for an oncology treatment. Here, this method provides an evaluation of patient data from an oncology treatment which is appliable to multiple treatment types (including radiotherapy and immune-checkpoint inhibitor therapy), and multiple types of outcome predictions (including adverse events, objective response rate, and the like).

At operation 1410, the flowchart 1400 begins with the selection or identification of one or more trained AI prediction models. These models may be trained (and validated) as discussed in the methods of FIGS. 2A-3B and FIG. 6. For instance, the model may be a trained AI prediction model that uses an extreme gradient boosting supervised machine learning algorithm, as discussed above. The AI prediction model may have been trained with training data that is specific to the human subject and a type of the oncology treatment, including with the use of data that is collected between treatment sessions of the oncology treatment. Likewise, the selection or identification of the AI prediction model may be based on successful validation or verification of the model after training, before use with the patient data. Such validation or verification may be based on one or more metrics including: accuracy, precision and recall, and a correlation coefficient (or, other metrics discussed above).

At operation 1420, patient data relevant to the oncology treatment is identified and/or received. The patient data may include the identification of electronic patient-recorded outcomes (ePROs) relating to an oncology treatment, as discussed above. For example, patient-reported outcomes may be provided from structured data collected in a questionnaire, to be filled out by a human subject, with such a questionnaire presenting a series of questions (or instructions) that is customized to the human subject. Also for example, patient-reported outcomes may be provided from unstructured data collected in one or more text inputs of such a questionnaire.

The patient data may also include other relevant medical data such as: clinical information of the human subject; laboratory data from one or more specimens collected from the human subject; treatment information from prior sessions of the oncology treatment delivered to the human subject; measurements from one or more wearable devices used by the human subject (directly from wearable devices or from smartphone activity/health data feeds); measurements from one or more medical monitoring devices external to the human subject; or event data from prior occurrence of adverse events by the human subject.

Other data associated with the human subject may be identified and used for AI-based modeling. For instance, this may include a subset of patient specific data that provides at least one physical characteristic independent of the oncology treatment (e.g., ethnicity, weight or other physical characteristics, medical history, age, sex, diet, genetics, medication, fitness). Other types of patient specific or patient related data may include discretionary clinical treatment plan preferences, treatment delivery equipment, patient demographics, and/or treatment facility (clinical) demographics. It will be understood that these characteristics and a variety of other profiling data on the human subject can be used to develop subsets of data for training and operation of the AI model(s).

At operation 1430, the patient data is provided to the trained AI prediction model as an input. At operation 1440, the patient data is processed with the trained AI prediction model, to produce a prediction of the treatment outcome. Then, at operation 1450, the prediction of the treatment outcome is output from the trained AI prediction model.

In an example, the prediction of the treatment outcome includes a prediction of one or more adverse events, and the prediction of each respective adverse event includes: a probability of an occurrence of the respective adverse event; and a timing and a severity of the respective adverse event, if the probability of the occurrence of the respective adverse event exceeds a defined amount. In another example, the prediction of the treatment outcome includes a prediction of an objective response rate of the human subject to the oncology treatment, and wherein the prediction of the objective response rate includes an indication or classification of a complete response or an amount of a partial response to the oncology treatment In a specific example, the one or more adverse events are radiotherapy adverse events, and the oncology treatment being analyzed is a radiotherapy treatment. In another specific example, the oncology treatment being analyzed is an immune checkpoint inhibitor therapy, and the one or more adverse events are immune-related adverse events.

At operation 1460, the treatment workflow of the oncology treatment is changed based on the prediction of the treatment outcome, which may be implemented using various commands or data outputs. In a scenario involving radiotherapy, modifying the treatment workflow includes changing a plan used for delivering the radiotherapy treatment to the human subject based on the radiotherapy adverse events. For instance, a timing, a dosage, or a location of the radiotherapy treatment, to be delivered with the plan, can be changed based on the prediction of the radiotherapy adverse events. In a scenario involving immune checkpoint inhibitor therapy, modifying the treatment workflow includes indicating a change to an amount or a timing of an immunotherapy treatment delivered to the human subject with the immune checkpoint inhibitor therapy. For instance, a change may be identified for an amount or a timing of an immunotherapy treatment to be delivered to the human subject with the immune checkpoint inhibitor therapy. In still another example, based on the prediction of the treatment outcome, a predicted dose delivery or efficacy of the oncology treatment is recalculated, followed by additional adaptive changes or data processing.

At operation 1470, the flowchart 1400 concludes with the output of information (e.g., data) related to the treatment outcome. Such an output may be provided in a visualization or interface, which is presented to the human subject or a clinician associated with the human subject, based on the prediction of the treatment outcome. The information may include one or more of: an alert, educational content, or a recommendation. In other examples, the output may provide a command or other electronic communication.

Figure 15:
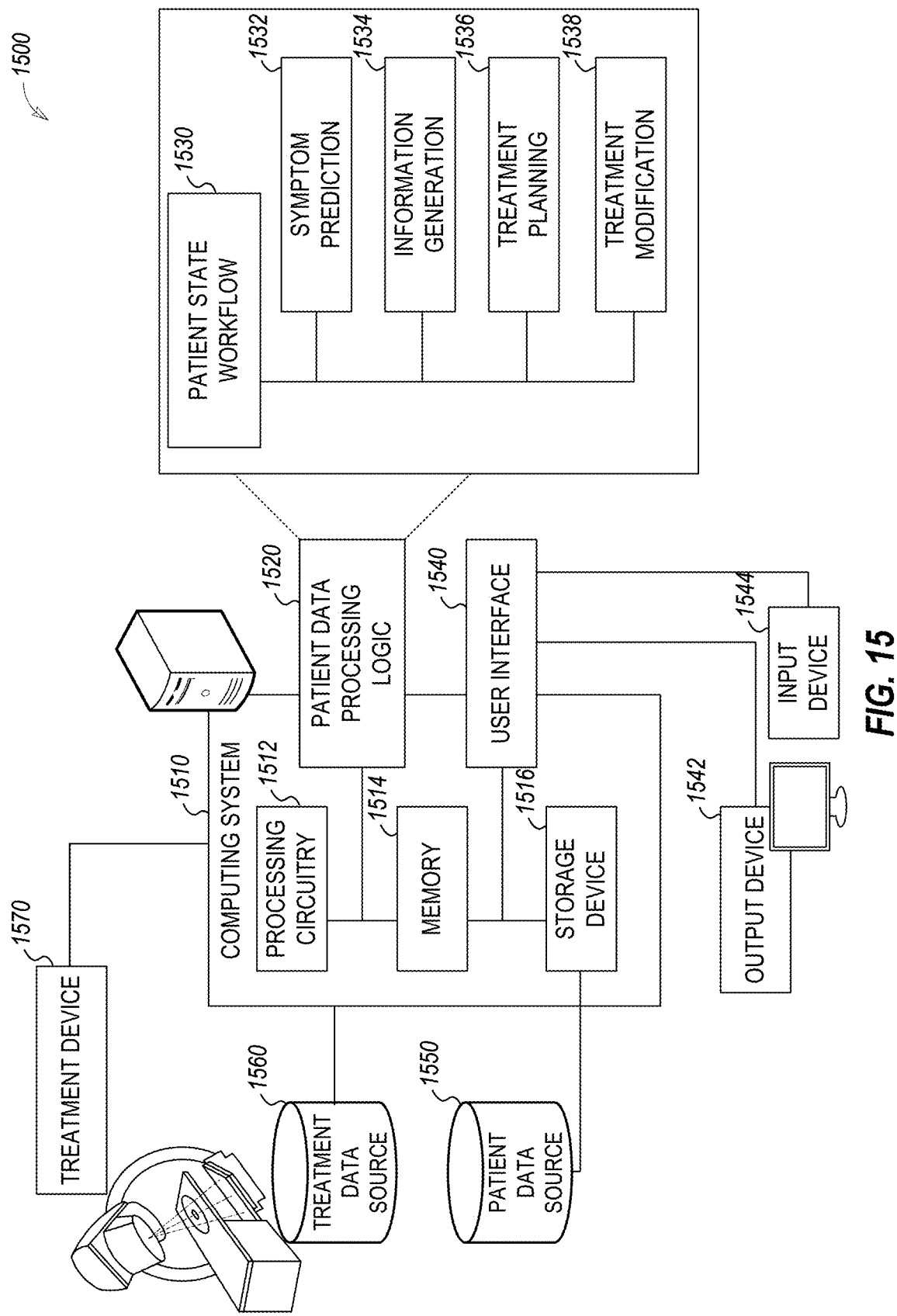
FIG. 15 illustrates a radiotherapy system, according to some examples.

FIG. 15 illustrates a radiotherapy system 1500 adapted for using machine learning models for assisting patient symptom prediction. The patient symptom prediction may be used to determine a more accurate patient state, to enable the radiotherapy system 1500 to modify or adapt radiation therapy to a human subject (e.g., a patient) based on nascent or developing medical conditions and symptoms.

The radiotherapy system includes a computing system 1510 which hosts patient data processing logic 1520. The computing system 1510 may be connected to a network (not shown), and such network may be connected to the Internet. For instance, a network can connect the computing system 1510 with one or more patient data sources 1550 (e.g., a radiology information system (RIS), a medical record system (e.g., an electronic medical record (EMR)/electronic health record (EHR) system), an oncology information system (OIS)), an image acquisition device (not shown), and a treatment device 1570 (e.g., a radiation therapy device). As an example, the computing system 1510 can be configured to perform operations by executing instructions or data from the patient data processing logic 1520, as part of operations to predict symptoms and customize radiation therapy treatment plans to be used by the treatment device 1570.

The computing system 1510 may include processing circuitry 1512, memory 1514, a storage device 1516, and other hardware and software-operable features such as a user interface 1540, communication interface, and the like. The storage device 1516 may store computer-executable instructions, such as an operating system, radiation therapy treatment plans (e.g., original treatment plans, adapted treatment plans, or the like), software programs (e.g., radiotherapy treatment plan software, artificial intelligence implementations such as machine learning models, deep learning models, and neural networks, etc.), and any other computer-executable instructions to be executed by the processing circuitry 1512.

In an example, the processing circuitry 1512 may include a processing device, such as one or more general-purpose processing devices such as a microprocessor, a central processing unit (CPU), a graphics processing unit (GPU), an accelerated processing unit (APU), or the like. More particularly, the processing circuitry 1512 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processing circuitry 1512 may also be implemented by one or more special-purpose processing devices such as an application specific integrated circuit (ASIC), a field programmable gate array (FPGA), a digital signal processor (DSP), a System on a Chip (SoC), or the like. As would be appreciated by those skilled in the art, in some examples, the processing circuitry 1512 may be a special-purpose processor, rather than a general-purpose processor. The processing circuitry 1512 may include one or more known processing devices, such as a microprocessor from the Pentium™, Core™, Xeon™, or Itanium® family manufactured by Intel™, the Turion™, Athlon™, Sempron™, Opteron™ FX™, Phenom™ family manufactured by AMD™, or any of various processors manufactured by Sun Microsystems. The processing circuitry 1512 may also include graphical processing units such as a GPU from the GeForce®, Quadro®, Tesla® family manufactured by Nvidia™, GMA, Iris™ family manufactured by Intel™, or the Radeon™ family manufactured by AMD™. The processing circuitry 1512 may also include accelerated processing units such as the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one processor, for example, a multi-core design or a plurality of processors each having a multi-core design. The processing circuitry 1512 can execute sequences of computer program instructions, stored in memory 1515, and accessed from the storage device 1516, to perform various operations, processes, and methods.

The memory 1515 may comprise read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a compact disc read-only memory (CD-ROM), a digital versatile disc (DVD) or other optical storage, a cassette tape, other magnetic storage device, or any other non-transitory medium that may be used to store information including image, data, or computer executable instructions (e.g., stored in any format) capable of being accessed by the processing circuitry 1512, or any other type of computer device. For instance, the computer program instructions can be accessed by the processing circuitry 1512, read from the ROM, or any other suitable memory location, and loaded into the RAM for execution by the processing circuitry 1512.

The storage device 1516 may constitute a drive unit that includes a machine-readable medium on which is stored one or more sets of instructions and data structures (e.g., software) embodying or utilized by any one or more of the methodologies or functions described herein (including, in various examples, the patient data processing logic 1520 and the user interface 1540). The instructions may also reside, completely or at least partially, within the memory 1514 and/or within the processing circuitry 1512 during execution thereof by the computing system 1510, with the memory 1514 and the processing circuitry 1512 also constituting machine-readable media.

The memory 1514 or the storage device 1516 may constitute a non-transitory computer-readable medium. For example, the memory 1514 or the storage device 1516 may store or load instructions for one or more software applications on the computer-readable medium. Software applications stored or loaded with the memory 1514 or the storage device 1516 may include, for example, an operating system for common computer systems as well as for software-controlled devices. The computing system 1510 may also operate a variety of software programs comprising software code for implementing the patient data processing logic 1520 and the user interface 1540. Further, the memory 1514 and the storage device 1516 may store or load an entire software application, part of a software application, or code or data that is associated with a software application, which is executable by the processing circuitry 1512. In a further example, the memory 1514 or the storage device 1516 may store, load, or manipulate one or more radiation therapy treatment plans, imaging data, patient state data, dictionary entries, artificial intelligence model data, labels, and mapping data, etc. It is contemplated that software programs may be stored not only on the storage device 1516 and the memory 1514 but also on a removable computer medium, such as a hard drive, a computer disk, a CD-ROM, a DVD, a HD-DVD, a Blu-Ray DVD, USB flash drive, a SD card, a memory stick, or any other suitable medium; such software programs may also be communicated or received over a network.

Although not depicted, the computing system 1510 may include a communication interface, network interface card, and communications circuitry. An example communication interface may include, for example, a network adaptor, a cable connector, a serial connector, a USB connector, a parallel connector, a high-speed data transmission adaptor (e.g., such as fiber optic, USB 3.0, thunderbolt, and the like), a wireless network adaptor (e.g., such as a IEEE 802.11/Wi-Fi adapter), a telecommunication adapter (e.g., to communicate with 3G, 4G/LTE, and 5G, networks and the like), and the like. Such a communication interface may include one or more digital and/or analog communication devices that permit a machine to communicate with other machines and devices, such as remotely located components, via a network. The network may provide the functionality of a local area network (LAN), a wireless network, a cloud computing environment (e.g., software as a service, platform as a service, infrastructure as a service, etc.), a client-server, a wide area network (WAN), and the like. For example, network may be a LAN or a WAN that may include other systems (including additional image processing computing systems or image-based components associated with medical imaging or radiotherapy operations).

In an example, the computing system 1510 may obtain patient data from the patient data source 1550, for hosting on the storage device 1516 and the memory 1514. The storage device 1516 and memory 1514 may store and host data to plan and optimize radiotherapy operations, including the image data, patient data, and other data required to create and implement a radiation therapy treatment plan and associated patient state estimation operations.

The processing circuitry 1512 may be communicatively coupled to the memory 1514 and the storage device 1516, and the processing circuitry 1512 may be configured to execute computer executable instructions stored thereon from either the memory 1514 or the storage device 1516. The processing circuitry 1512 may execute instructions to cause medical information from the patient data source 1550 to be received or obtained in memory 1514, and processed using the patient data processing logic 1520. In some examples, one or more of the systems may form a distributed computing/simulation environment that uses a network to collaboratively perform the embodiments described herein (such as in an edge computing environment). In addition, such network may be connected to the Internet to communicate with servers and clients that reside remotely on the Internet.

In further examples, the processing circuitry 1512 may utilize software programs (e.g., a treatment planning software) along with the patient data sources 1550 and image data to create a radiation therapy treatment plan maintained in the treatment data source 1560. In an example, the image data may include 2D or 3D volume imaging, such as from a CT or MR. In addition, the processing circuitry 1512 may utilize aspects of AI such as machine learning, deep learning, and neural networks to generate or control various aspects of the treatment plan, including in response to predicted symptoms or outcomes.

For instance, such software programs may utilize patient data processing logic 1520 to implement a patient state determination workflow 1550, using the techniques further discussed herein. The processing circuitry 1512 may subsequently then modify and transmit the executable radiation therapy treatment plan via a communication interface and the network to the treatment device 1580, where the radiation therapy plan will be used to treat a patient with radiation via the treatment device, consistent with results of the patient state determination workflow 1530. Other outputs and uses of the software programs and the patient state determination workflow 1530 may occur with use of the computing system 1510. As discussed further below, the processing circuitry 1512 may execute a software program that invokes the patient data processing logic 1520 to implement functions including aspects of image processing and registration, feature extraction, machine learning model processing, and the like.

In an example, an image acquisition device may be integrated with the treatment device 1570 as a single apparatus (e.g., an MRI device combined with a linear accelerator, also referred to as an "MR-LINAC"). Such an MR-LINAC can be used, for example, to precisely determine a location of a target organ or a target tumor in the human subject (i.e., the patient), so as to direct radiation therapy accurately according to the radiation therapy treatment plan to a predetermined target. For instance, a radiation therapy treatment plan may provide information about a particular radiation dose to be applied to each patient. The radiation therapy treatment plan may also include other radiotherapy information, such as beam angles, dose-histogram-volume information, the number of radiation beams to be used during therapy, the dose per beam, and the like.

The computing system 1510 may communicate with an external database through a network to send/receive a plurality of various types of data related to image processing and radiotherapy operations. For example, an external database may include machine data that is information associated with the treatment device 1570, an image acquisition device, or other machines relevant to radiotherapy or medical procedures. Machine data information may include radiation beam size, arc placement, beam on and off time duration, machine parameters, segments, multi-leaf collimator (MLC) configuration, gantry speed, MM pulse sequence, and the like. The external database may be a storage device and may be equipped with appropriate database administration software programs. Further, such databases or data sources may include a plurality of devices or systems located either in a central or a distributed manner.

The computing system 1510 can collect and obtain data, and communicate with other systems, via a network using one or more communication interfaces, which are communicatively coupled to the processing circuitry 1512 and the memory 1514. For instance, a communication interface may provide communication connections between the computing system 1510 and radiotherapy system components (e.g., permitting the exchange of data with external devices). For instance, the communication interface may in some examples have appropriate interfacing circuitry from an output device 1542 or an input device 1544 to connect to the user interface 1540, which may be a hardware keyboard, a keypad, or a touch screen through which a user may input information into the radiotherapy system 1500.

As an example, the output device 1542 may include a display device which outputs a representation of the user interface 1540 and one or more aspects, visualizations, or representations of the medical images. The output device 1542 may include one or more display screens that display medical images, interface information, treatment planning parameters (e.g., contours, dosages, beam angles, labels, maps, etc.) treatment plans, a target, localizing a target or tracking a target, patient state estimations (e.g., a 3D volume), or any related information to the user. The input device 1544 connected to the user interface 1540 may be a keyboard, a keypad, a touch screen or any type of device that a user may input information to the radiotherapy system 1500. Alternatively, the output device 1542, the input device 1544, and features of the user interface 1540 may be integrated into a single device such as a smartphone or tablet computer, e.g., Apple iPad®, Lenovo Thinkpad®, Samsung Galaxy®, etc.

Furthermore, many components of the radiotherapy system 1500 may be implemented with a virtual machine (e.g., via VMWare, Hyper-V, and the like virtualization platforms). For instance, a virtual machine can be software that functions as hardware. Therefore, a virtual machine can include at least one or more virtual processors, one or more virtual memories, and one or more virtual communication interfaces that together function as hardware. For example, the computing system 1510 or like components may be implemented as a virtual machine or within a cloud-based virtualization environment.

The patient data processing logic 1520 or other software programs may cause the computing system to communicate with the patient data sources 1550 to read data into memory 1514 and the storage device 1516, or store data values from the memory 1514 or the storage device 1516 to and from the patient data sources 1550. Although such patient data sources 1550 may include patient-reported data and clinical data suggested above, other types of data may also be included and analyzed.

The patient data processing logic 1520 in the computing system 1510 is depicted as implementing a patient state workflow 1530 with various aspects of prediction or estimation of a patient state provided by models or algorithms. In an example, the patient state workflow 1530 analyzes the input patient data (symptoms, clinical data), with symptom prediction 1532 functions to estimate a patient state and predict upcoming symptoms from a radiotherapy session. In a further example, the patient state workflow 1530 uses the predicted symptoms to generate or select information with information generation functions 1534, such as to provide information to a patient or clinician when a threshold of particular symptoms is detected.

The patient state workflow 1530 further involves aspects of treatment planning 1536 and treatment modification 1538, based on the predicted symptoms. Such treatment planning 1536 and treatment modification 1538 may produce data that is used to control a treatment plan, the treatment device 1580 or other aspects of the radiotherapy session.

Figure 16:
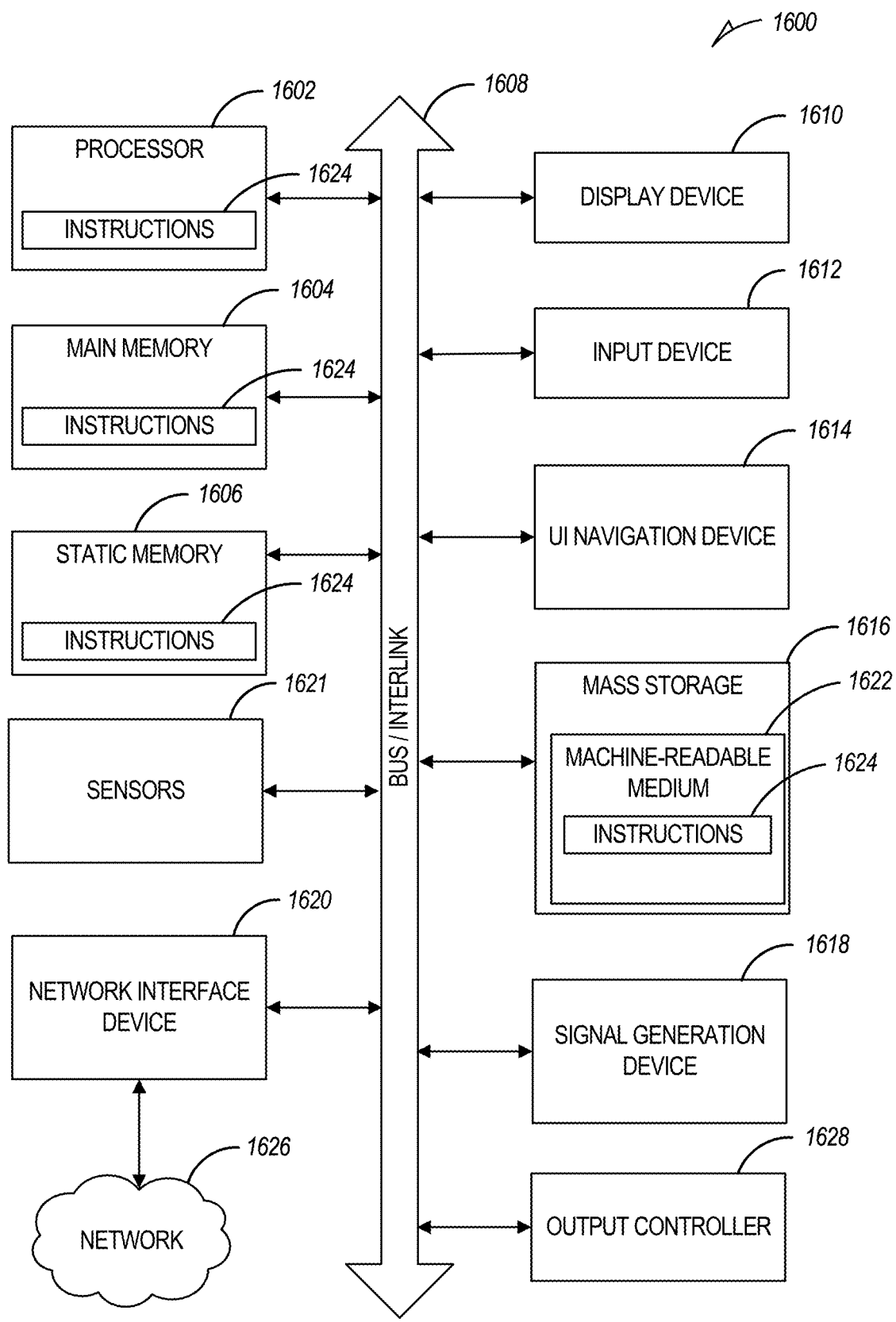
FIG. 16 illustrates an exemplary block diagram of a machine on which one or more of the methods as discussed herein can be implemented.

FIG. 16 illustrates a block diagram of an example of a machine 1600 on which one or more of the methods as discussed herein can be implemented. In one or more examples, one or more items of the computing system 1510 can be implemented by the machine 1600. In alternative examples, the machine 1600 operates as a standalone device or may be connected (e.g., networked) to other machines. In one or more examples, the computing system 1510 can include one or more of the items of the machine 1600. In a networked deployment, the machine 1600 may operate in the capacity of a server or a client machine in server-client network environment, or as a peer machine in a peer-to-peer (or distributed) network environment. The machine may be a personal computer (PC), server, a tablet, smartphone, a web appliance, edge computing device, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example machine 1600 includes processing circuitry or processor 1602 (e.g., a CPU, a graphics processing unit (GPU), an ASIC, circuitry, such as one or more transistors, resistors, capacitors, inductors, diodes, logic gates, multiplexers, buffers, modulators, demodulators, radios (e.g., transmit or receive radios or transceivers), sensors 1621 (e.g., a transducer that converts one form of energy (e.g., light, heat, electrical, mechanical, or other energy) to another form of energy), or the like, or a combination thereof), a main memory 1604 and a static memory 1606, which communicate with each other via a bus 1608. The machine 1600 (e.g., computer system) may further include a video display device 1610 (e.g., a liquid crystal display (LCD) or a cathode ray tube (CRT)). The machine 1600 also includes an alphanumeric input device 1612 (e.g., a keyboard), a user interface (UI) navigation device 1614 (e.g., a mouse), a disk drive or mass storage unit 1616, a signal generation device 1618 (e.g., a speaker), and a network interface device 1620.

The disk drive unit 1616 includes a machine-readable medium 1622 on which is stored one or more sets of instructions and data structures (e.g., software) 1624 embodying or utilized by any one or more of the methodologies or functions described herein. The instructions 1624 may also reside, completely or at least partially, within the main memory 1604 and/or within the processor 1602 during execution thereof by the machine 1600, the main memory 1604 and the processor 1602 also constituting machine-readable media.

The machine 1600 as illustrated includes an output controller 1628. The output controller 1628 manages data flow to/from the machine 1600. The output controller 1628 is sometimes called a device controller, with software that directly interacts with the output controller 1628 being called a device driver.

While the machine-readable medium 1622 is shown in an example to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present disclosure, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), EEPROM, and flash memory devices; magnetic disks such as internal hard disks and removable disks; magneto-optical disks; and CD-ROM and DVD-ROM disks.

The instructions 1624 may further be transmitted or received over a communications network 1626 using a transmission medium. The instructions 1624 may be transmitted using the network interface device 1620 and any one of a number of well-known transfer protocols (e.g., HTTP). Examples of communication networks include a LAN, a WAN, the Internet, mobile telephone networks, Plain Old Telephone (POTS) networks, and wireless data networks (e.g., Wi-Fi and 4G/5G data networks). The term "transmission medium" shall be taken to include any intangible medium that is capable of storing, encoding or carrying instructions for execution by the machine, and includes digital or analog communications signals or other intangible media to facilitate communication of such software.

As used herein, "communicatively coupled between" means that the entities on either of the coupling must communicate through an item therebetween and that those entities cannot communicate with each other without communicating through the item.

Additional Notes

The above detailed description includes references to the accompanying drawings, which form a part of the detailed description. The drawings show, by way of illustration but not by way of limitation, specific embodiments in which the disclosure can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements of aspects of the disclosure or in the embodiments thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

Embodiments of the disclosure may be implemented with computer-executable instructions. The computer-executable instructions (e.g., software code) may be organized into one or more computer-executable components or modules. Aspects of the disclosure may be implemented with any number and organization of such components or modules. For example, aspects of the disclosure are not limited to the specific computer-executable instructions or the specific components or modules illustrated in the figures and described herein. Other embodiments of the disclosure may include different computer-executable instructions or components having more or less functionality than illustrated and described herein.

Method examples (e.g., operations and functions) described herein can be machine or computer-implemented at least in part (e.g., implemented as software code or instructions). Some examples can include a computer-readable medium or machine-readable medium encoded with instructions operable to configure an electronic device to perform methods as described in the above examples. An implementation of such methods can include software code, such as microcode, assembly language code, a higher-level language code, or the like (e.g., "source code"). Such software code can include computer-readable instructions for performing various methods (e.g., "object" or "executable code"). The software code may form portions of computer program products. Software implementations of the embodiments described herein may be provided via an article of manufacture with the code or instructions stored thereon, or via a method of operating a communication interface to send data via a communication interface (e.g., wirelessly, over the internet, via satellite communications, and the like).

Further, the software code may be tangibly stored on one or more volatile or non-volatile computer-readable storage media during execution or at other times. These computer-readable storage media may include any mechanism that stores information in a form accessible by a machine (e.g., computing device, electronic system, and the like), such as, but are not limited to, floppy disks, hard disks, removable magnetic disks, any form of magnetic disk storage media, CD-ROMS, magnetic-optical disks, removable optical disks (e.g., compact disks and digital video disks), flash memory devices, magnetic cassettes, memory cards or sticks (e.g., secure digital cards), RAMs (e.g., CMOS RAM and the like), recordable/non-recordable media (e.g., read only memories (ROMs)), EPROMS, EEPROMS, or any type of media suitable for storing electronic instructions, and the like. Such computer-readable storage medium is coupled to a computer system bus to be accessible by the processor and other parts of the OIS.

In various embodiments of the disclosure, the method of creating a component or module can be implemented in software, hardware, or a combination thereof. The methods provided by various embodiments of the present disclosure, for example, can be implemented in software by using standard programming languages such as, for example, C, C++, C#, Java, Python, CUDA programming, and the like; and combinations thereof. As used herein, the terms "software" and "firmware" are interchangeable, and include any computer program stored in memory for execution by a computer.

A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present disclosure also relates to a system for performing the operations herein. This system may be specially constructed for the required purposes, or it may comprise a general purpose computer selectively activated or reconfigured by a computer program stored in the computer. The order of execution or performance of the operations in embodiments of the disclosure illustrated and described herein is not essential, unless otherwise specified. That is, the operations may be performed in any order, unless otherwise specified, and embodiments of the disclosure may include additional or fewer operations than those disclosed herein. For example, it is contemplated that executing or performing a particular operation before, contemporaneously with, or after another operation is within the scope of aspects of the disclosure.

What is claimed is:

1. A method for generating a predicted treatment outcome of an oncology treatment for a human subject, the method comprising:
   receiving patient data for the human subject, the patient data including patient-reported outcomes relating to the oncology treatment that are collected from the human subject;
   processing the patient data with a trained artificial intelligence (AI) prediction model, the trained AI prediction model configured to receive the patient data as an input and to produce a prediction of a treatment outcome for the human subject as an output; and
   outputting data, based on the prediction of the treatment outcome, to either: (i) modify a treatment workflow of the oncology treatment for the human subject, or (ii) recalculate a predicted dose delivery or efficacy of the oncology treatment for the human subject;
   wherein the prediction of the treatment outcome includes a prediction of one or more adverse events, and wherein the prediction of each respective adverse event includes:
      a probability of an occurrence of the respective adverse event; and
      a timing or a severity of the respective adverse event, if the probability of the occurrence of the respective adverse event exceeds a defined amount.

2. The method of claim 1, wherein the one or more adverse events are radiotherapy adverse events, wherein the oncology treatment is a radiotherapy treatment, and wherein the data to modify the treatment workflow includes a command to change a plan used for delivering the radiotherapy treatment to the human subject based on the radiotherapy adverse events.

3. The method of claim 2, wherein a timing, a dosage, or a location of the radiotherapy treatment, to be delivered with the plan, is changed based on the prediction of the radiotherapy adverse events.

4. The method of claim 1, wherein the prediction of one or more adverse events is based on the processing of the patient data with the trained AI prediction model, using at least one subset of patient data including data related to:
   at least one physical characteristic independent of the oncology treatment, provided from among: ethnicity, weight or other physical characteristics, medical history, age, sex, diet, genetics, medication, or fitness;
   discretionary clinical treatment plan preferences;
   delivery equipment;
   patient demographics; or
   clinical demographics.

5. The method of claim 1, wherein the one or more adverse events are immune-related adverse events, wherein the oncology treatment is an immune checkpoint inhibitor therapy, and wherein the data to modify the treatment workflow includes a command to change an amount or a timing of an immunotherapy treatment delivered to the human subject with the immune checkpoint inhibitor therapy.

6. The method of claim 1, wherein the prediction of the treatment outcome includes a prediction of an objective response rate of the human subject to the oncology treatment, and wherein the prediction of the objective response rate includes a classification of a complete response or an amount of a partial response to the oncology treatment.

7. The method of claim 1, wherein the patient-reported outcomes are provided from structured data collected in a questionnaire, and wherein the questionnaire provides a series of questions that are customized to the human subject.

8. The method of claim 7, wherein the patient-reported outcomes are also provided from unstructured data collected in one or more text inputs of the questionnaire.

9. The method of claim 1, wherein the patient data further includes one or more of:
   clinical information of the human subject;
   laboratory data from one or more specimens collected from the human subject;
   treatment information from prior sessions of the oncology treatment delivered to the human subject;
   measurements from one or more wearable devices used by the human subject;
   measurements from one or more medical monitoring devices external to the human subject; or
   event data from prior occurrence of adverse events by the human subject.

10. The method of claim 9, further comprising:
    verifying performance of the trained AI prediction model after training, and before use with the patient data, based on metrics including one or more of: accuracy, precision and recall, or a correlation coefficient.

11. The method of claim 1, wherein the trained AI prediction model uses an extreme gradient boosting supervised machine learning algorithm.

12. The method of claim 1, wherein the trained AI prediction model is trained with training data that is specific to the human subject and a type of the oncology treatment, and wherein the patient data is collected between treatment sessions of the oncology treatment.

13. The method of claim 1, wherein processing the patient data with the trained AI prediction model includes use of multiple AI prediction models to produce the output, and wherein each of the multiple AI prediction models is customized to a respective symptom or respective outcome associated with the oncology treatment.

14. The method of claim 1, further comprising:
    outputting information related to the treatment outcome to the human subject or a clinician associated with the human subject, based on the prediction of the treatment outcome, wherein the information includes one or more of: an alert, educational content, or a recommendation.

15. A method of dynamically adapting a radiotherapy treatment plan having multiple fractions, based on a predicted treatment outcome of an oncology treatment for a human subject, the method comprising:
    developing a treatment workflow for the oncology treatment for the human subject based on clinically determined expected outcomes of such treatment;
    generating the predicted treatment outcome of the oncology treatment for the human subject;
    receiving intra-fraction patient data for the human subject, the patient data including patient-reported outcomes relating to the oncology treatment that are collected from the human subject;

processing the patient data with a trained artificial intelligence (AI) prediction model, the trained AI prediction model configured to receive the intra-fraction patient data as an input and to produce a prediction of a treatment outcome for the human subject as an output;

comparing the predicted treatment outcome to an expected treatment outcome; and changing the treatment workflow based on the comparison of the predicted treatment outcome, in response to determining that a difference between the predicted treatment outcome and the expected treatment outcome is outside of a predetermined tolerance.

16. The method of claim 15, wherein the patient-reported outcomes are utilized as an input for changing the treatment workflow.

17. A method of monitoring efficacy of a treatment plan of a radiotherapy treatment for a human subject comprising:

processing the treatment plan with a trained artificial intelligence (AI) prediction model, the trained AI prediction model configured to receive data for the treatment plan as an input and to produce an adverse effect prediction report of potential adverse patient-reported outputs associated with the treatment plan indicative of ineffective treatment for the human subject as an output;

receiving patient data for the human subject, the patient data including patient-reported outcomes relating to the treatment plan that are collected from the human subject; and monitoring for predicted adverse patient-reported outputs and, where identified, outputting data indicative that the treatment plan may require adjustment.

18. The method of claim 17, wherein the output data is used to determine whether delivery efficacy of the treatment plan is outside of acceptable parameters.

19. The method of claim 17, wherein the output data includes data to modify a treatment workflow of the radiotherapy treatment for the human subject, based on a prediction of one or more outcomes of the radiotherapy treatment.

20. A non-transitory computer-readable storage medium comprising computer-readable instructions for generating a predicted treatment outcome of an oncology treatment for a human subject, wherein the instructions, when executed, cause a computing machine to perform operations comprising:

receiving patient data for the human subject, the patient data including patient-reported outcomes relating to the oncology treatment that are collected from the human subject;

processing the patient data with a trained artificial intelligence (AI) prediction model, the trained AI prediction model configured to receive the patient data as an input and to produce a prediction of a treatment outcome for the human subject as an output; and outputting data to modify a treatment workflow of the oncology treatment for the human subject, based on the prediction of the treatment outcome;

wherein the prediction of the treatment outcome includes a prediction of one or more adverse events, and wherein the prediction of each respective adverse event includes:

a probability of an occurrence of the respective adverse event; and a timing or a severity of the respective adverse event, if the probability of the occurrence of the respective adverse event exceeds a defined amount.

21. The computer-readable storage medium of claim 20, wherein the one or more adverse events are radiotherapy adverse events, wherein the oncology treatment is a radiotherapy treatment, and wherein the data to modify the treatment workflow includes a command to change a plan used for delivering the radiotherapy treatment to the human subject based on the radiotherapy adverse events.

22. The computer-readable storage medium of claim 21, wherein a timing, a dosage, or a location of the radiotherapy treatment, to be delivered with the plan, is changed based on the prediction of the radiotherapy adverse events.

23. The computer-readable storage medium of claim 20, wherein the one or more adverse events are immune-related adverse events, wherein the oncology treatment is an immune checkpoint inhibitor therapy, and wherein the data to modify the treatment workflow includes a command to change an amount or a timing of an immunotherapy treatment delivered to the human subject with the immune checkpoint inhibitor therapy.

24. The computer-readable storage medium of claim 20, wherein the prediction of the treatment outcome includes a prediction of an objective response rate of the human subject to the oncology treatment, and wherein the prediction of the objective response rate includes a classification of a complete response or an amount of a partial response to the oncology treatment.

25. The computer-readable storage medium of claim 20, wherein the patient-reported outcomes are provided from structured data collected in a questionnaire, and wherein the questionnaire provides a series of questions that is customized to the human subject.

26. The computer-readable storage medium of claim 25, wherein the patient-reported outcomes are also provided from unstructured data collected in one or more text inputs of the questionnaire.

27. The computer-readable storage medium of claim 20, wherein the patient data further includes one or more of:

clinical information of the human subject;

laboratory data from one or more specimens collected from the human subject;

treatment information from prior sessions of the oncology treatment delivered to the human subject;

measurements from one or more wearable devices used by the human subject;

measurements from one or more medical monitoring devices external to the human subject; or event data from prior occurrence of adverse events by the human subject.

28. The computer-readable storage medium of claim 20, wherein the trained AI prediction model uses an extreme gradient boosting supervised machine learning algorithm.

29. The computer-readable storage medium of claim 28, wherein the instructions further cause the computing machine to perform operations comprising:

verifying performance of the trained AI prediction model after training, and before use with the patient data, based on metrics including one or more of: accuracy, precision and recall, or a correlation coefficient.

30. The computer-readable storage medium of claim 20, wherein the trained AI prediction model is trained with training data that is specific to the human subject and a type of the oncology treatment, and wherein the patient data is collected between treatment sessions of the oncology treatment.

31. The computer-readable storage medium of claim 20, wherein processing the patient data with the trained AI prediction model includes use of multiple AI prediction models to produce the output, and wherein each of the multiple AI prediction models is customized to a respective symptom or respective outcome associated with the oncology treatment.

32. The computer-readable storage medium of claim 20, wherein the instructions further cause the computing machine to perform operations comprising:
  outputting information related to the treatment outcome to the human subject or a clinician associated with the human subject, based on the prediction of the treatment outcome, wherein the information includes one or more of:
  an alert, educational content, or a recommendation.

* * * * *